United States Patent [19]

Faustini et al.

[11] Patent Number: 4,543,353
[45] Date of Patent: Sep. 24, 1985

[54] ESTER AND AMIDE DERIVATIVES OF 13,14-DIDEHYDRO PROSTAGLANDINS

[75] Inventors: Franco Faustini, Milan; Vittoria Villa, Briosco; Carmelo Gandolfi, Milan; Enrico Di Salle, Milan, all of Italy

[73] Assignee: Farmitalia Carlo Erba S.p.A., Milan, Italy

[21] Appl. No.: 436,419

[22] Filed: Oct. 25, 1982

[30] Foreign Application Priority Data

Nov. 27, 1981 [GB] United Kingdom ................. 8135799

[51] Int. Cl.$^4$ ................... C07C 177/00; A61K 31/557
[52] U.S. Cl. ..................................... 514/236; 514/255; 514/317; 514/399; 514/530; 544/399; 544/171; 546/239; 548/341; 560/107; 560/118
[58] Field of Search ................ 560/118, 107; 548/341; 546/239; 544/171, 399; 424/305, 248.55, 250, 273 R, 274

[56] References Cited

U.S. PATENT DOCUMENTS 3,935,254 1/1976 Gandolfi ............................. 562/503
4,035,415 7/1977 Gandolfi ............................. 562/503

Primary Examiner—Robert Gerstl
Attorney, Agent, or Firm—Murray, Whisenhunt and Ferguson

[57] ABSTRACT

Esters of 13,14-didehydro prostaglandins have been prepared.

7 Claims, No Drawings

ESTER AND AMIDE DERIVATIVES OF 13,14-DIDEHYDRO PROSTAGLANDINS

The invention relates to new 13,14-didehydro prostaglandins, to a process for their preparation, to pharmaceutical and veterinary compositions containing them and to certain intermediates useful for the preparation of the said compounds. The invention provides optically active or racemic prostaglandin derivatives of formula (I)

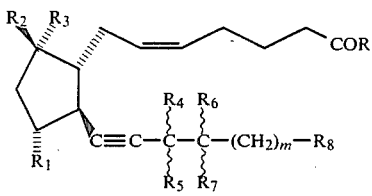

wherein
R is

wherein each of R' and R", independently, represents hydrogen, $C_1$–$C_6$ alkyl, aryl or heterocyclyl or R' and R", taken together with the nitrogen atom to which they are linked, form a heterocyclic radical; or R is —Y—$(CH_2)_n$—Z, wherein Y is —O— or —NH—, n is an integer of 1 to 4 and Z represents either a group

wherein R' and R" are as defined above or a group —OR''', wherein R''' is $C_1$–$C_6$ alkyl or a cycloalkyl, aryl or heterocyclic ring;
the symbol ≗ represents a single or a double bond, wherein, when the symbol ≗ is a double bond, $R_1$ is a hydrogen atom and $R_2$ and $R_3$, taken together, form an oxo group and, when the symbol ≗ is a single bond, $R_1$ is hydroxy, $R_2$ is hydrogen and $R_3$ is hydroxy or acyloxy or $R_2$ and $R_3$, taken together, form an oxo group;
one of $R_4$ and $R_5$ is hydroxy and the other is hydrogen;
each of $R_6$ and $R_7$ represents, independently, hydrogen, $C_1$–$C_4$ alkyl or fluorine;
m is zero, 1, 2 or 3; and
$R_8$ is
  (a) $C_1$–$C_4$ alkyl;
  (b) a $C_3$–$C_7$ cycloalkyl ring unsubstituted or substituted by one or more substituents chosen from halogen, trihalo-$C_1$–$C_6$ alkyl, $C_1$–$C_4$ alkyl, $C_1$–$C_4$ alkoxy, phenyl and phenoxy;
  (c) a phenyl ring unsubstituted or substituted by one or more substituents chosen from (a') $C_1$–$C_6$ alkyl; (b') $C_1$–$C_6$ alkoxy; (c') trihalo-$C_1$–$C_6$ alkyl; (d') halogen; (e')

wherein each of $R_9$ and $R_{10}$ is independently chosen from hydrogen, phenyl, benzoyl, $C_1$–$C_6$ alkyl, and $C_1$–$C_6$ aliphatic acyl; (f') phenyl unsubstituted or substituted by one or more substituents chosen from $C_1$–$C_6$ alkoxy and halogen; and (g') phenoxy unsubstituted or substituted by one or more substituents chosen from $C_1$–$C_6$ alkoxy and halogen; and
  (d) a heterocyclic ring unsubstituted or substituted by one or more substituents chosen from halogen, trihalo-$C_1$–$C_6$ alkyl, $C_1$–$C_4$ alkyl, $C_1$–$C_4$ alkoxy, phenyl and phenoxy;
provided that, when R is a group

wherein R' and R" are as defined above, $R_8$ is $C_1$–$C_4$ alkyl only; and the pharmaceutically or veterinarily acceptable salts thereof.

The compounds and the salts of the present invention have the advantage that they are more potent, in particular when administered parenterally, and have also more lasting activity, in particular when administered orally, than related compounds disclosed in the prior art, in particular those specifically disclosed in U.S. Pat. No. 3,935,254 and British Pat. No. 2,009,145B.

The formula reported above for the compounds covered by this invention includes all possible isomers, in particular, stereoisomers as well as their mixtures, for example mixtures of epimers. The double bond in 5(6) is a cis double bond. In the formulae of this invention, dashed lines ( ⦀⦀⦀ ) indicate that the substituents are in the α-configuration, that is, beneath the plane of the ring or, of a side chain. Wedges (◀) indicate that the substituents are in the β-configuration, that is, above the plane of the ring, or of a side chain. Wavy lines ( ∼ ) indicate that the groups, when the carbon atom to which they are bound is asymmetric, may be both in the α- or β-configuration and in the (α-,β-) configuration, that is a mixture of the two epimers. For example the hydroxy group bound to the carbon atom in position 15 may be in configuration (α), (β) and (α,β), that is, a mixture of 15(α)- and 15(β)-epimers. In the same way, when the carbon atom in the position 16 has two different substituents, these may be 16(α)-, 16(β)- and 16(α,β), that is a mixture of the two 16(α)- and 16(β)-diastereoisomers.

The symbols (S) and (R) of each chiral center are assigned according to the sequence rule arranging the ligands in order of decreasing atomic number.

The alkyl, alkoxy and trihaloalkyl groups can be straight or branched chains.

The term $C_1$–$C_6$ aliphatic acyl refers to groups derived from carboxylic acids such as formyl, acetyl, propionyl, butyryl, valeryl and isovaleryl.

A halogen atom is, preferably, fluorine, chlorine or bromine. When one or both of R' and R" are $C_1$–$C_6$ alkyl, they are preferably methyl, ethyl, propyl or butyl.

When R''' and/or one or both of R' and R'' are heterocyclyl, the heterocyclic ring is preferably chosen from pyrrolyl, imidazolyl, pyrazolyl, pyridyl, pyrazinyl, imidazolinyl, imidazolidinyl, pyrazolinyl, piperidyl, piperazinyl and morpholinyl. An aryl group is preferably phenyl.

When R' and R'', taken together with the nitrogen atom to which they are linked form a heterocyclic radical, this radical is preferably chosen from imidazolinyl, imidazolidinyl, pyrazolinyl, piperidino, piperazinyl, morpholino and pyrazolidinyl. R', R'' and R''' as individual heterocyclic groups can also be piperidino or morpholino.

When R''' is $C_1$-$C_6$ alkyl it is preferably methyl, ethyl, propyl or butyl.

When R''' is a cycloalkyl ring it is preferably a $C_3$-$C_7$ monocycloalkyl ring, more preferably cyclopentyl, cyclohexyl or cycloheptyl.

When $R_3$ is acyloxy, this is preferably a benzoyloxy group or a $C_2$-$C_6$ alkanoyloxy group, for example, acetoxy or propionyloxy.

When one or both of $R_6$ and $R_7$ are $C_1$-$C_4$ alkyl, they are preferably methyl or ethyl.

When $R_8$ is $C_1$-$C_4$ alkyl it is preferably methyl, ethyl or propyl.

When $R_8$ is a $C_3$-$C_7$ cycloalkyl ring unsubstituted or substituted as described above under (b), it is preferably cyclopentyl, cyclohexyl or cycloheptyl.

When $R_8$ is a phenyl ring unsubstituted or substituted as described above under (c), the ring is preferably substituted by one or more substituents chosen from methyl, methoxy, trifluoromethyl, fluorine, chlorine, iodine and

wherein $R_9$ and $R_{10}$ are as defined above.

More preferably, when $R_8$ is a phenyl ring substituted by

each of $R_9$ and $R_{10}$ is independently chosen from hydrogen and $C_1$-$C_6$ alkyl or one of $R_9$ and $R_{10}$ is hydrogen or $C_1$-$C_6$ alkyl and the other is $C_1$-$C_6$ aliphatic acyl.

When $R_8$ is a heterocyclic ring unsubstituted or substituted as described above under (d) it may be either a heteromonocyclic ring or a heterobicyclic ring and contains at least one heteroatom selected from N, S and O.

Examples of preferred heteromonocyclic radicals are tetrahydrofuryl, tetrahydropyranyl, pyrrolyl, pyrazolyl, oxazolyl, isoxazolyl, pyridyl, pyrazinyl, pyrimidinyl, pyridazinyl. Examples of preferred heterobicyclic radicals are 2-oxabicyclo[3.3.0]octyl, 2-oxabicyclo[3.4.0]nonyl, 2-thiabicyclo[3.3.0]octyl, 2-thiabicyclo[3.4.0]nonyl and their unsaturated analogs.

Preferred compounds of the invention are the compounds of formula (I), wherein
R is

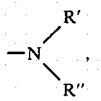

wherein R' and R'' are as defined above; the symbol is a single bond, $R_1$ is hydroxy, $R_2$ is hydrogen and $R_3$ is hydroxy or acyloxy, or $R_2$ and $R_3$, taken together are an oxo group; or the symbol is a double bond, $R_1$ is a hydrogen atom and $R_2$ and $R_3$, taken together, form an oxo group;

one of $R_4$ and $R_5$ is hydroxy and the other is hydrogen;

each of $R_6$ and $R_7$ represents, independently, hydrogen, $C_1$-$C_4$ alkyl or fluorine;

m is as defined above;

$R_8$ is $C_1$-$C_4$ alkyl;

and the pharmaceutically or veterinarily acceptable salts thereof. Preferred compounds of the invention are also the compounds of formula (I) wherein R is —Y—$(CH_2)_n$—Z, wherein Y, n and Z are as defined above; the symbol $\text{---}$ represents a single bond, $R_1$ is hydroxy, $R_2$ is hydrogen and $R_3$ is hydroxy or acyloxy, or $R_2$ and $R_3$, taken together, form an oxo group; or the symbol $\text{---}$ represents a double bond, $R_1$ is a hydrogen atom and $R_2$ and $R_3$, taken together, form an oxo group;

one of $R_4$ and $R_5$ is hydroxy and the other is hydrogen;

each of $R_6$ and $R_7$ represents, independently, hydrogen, $C_1$-$C_4$ alkyl or fluorine;

m is zero, 1 or 2;

$R_8$ represents $C_1$-$C_4$ alkyl; a cyclopentyl, cyclohexyl or cycloheptyl ring wherein each ring is unsubstituted or substituted by one or more substituents chosen from halogen, trihalo-$C_1$-$C_6$ alkyl, $C_1$-$C_4$ alkyl, $C_1$-$C_4$ alkoxy, phenyl and phenoxy; a phenyl ring unsubstituted or substituted by one or more substituents chosen from (a') to (g') as reported above; or a pyrrolyl, pyrazolyl, pyridyl or pyrazinyl ring, where each ring is unsubstituted or substituted by one or more substituents chosen from $C_1$-$C_4$ alkyl and $C_1$-$C_4$ alkoxy; and the pharmaceutically or veterinarily acceptable salts thereof.

More preferred compounds of the invention are the compounds of formula (I), wherein R is —Y—$(CH_2)_n$—Z, wherein Y is —O—, n is 1, 2 or 3, and Z is either a group

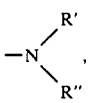

wherein R' and R'', taken together with the nitrogen atom to which they are linked, form a radical chosen from imidazolinyl, imidazolidinyl, pyrazolinyl, piperidino, piperazinyl and morpholino, or Z is a group —OR''', wherein R''' is $C_1$-$C_6$ alkyl;

the symbol $\text{===}$ represents a single bond, $R_1$ is hydroxy, $R_2$ is hydrogen and $R_3$ is hydroxy or acyloxy, or $R_2$ and $R_3$, taken together form an oxo group; or the symbol $\text{===}$ represents a double bond, $R_1$ is a hydrogen atom and $R_2$ and $R_3$ taken together form an oxo group;

one of $R_4$ and $R_5$ is hydroxy and the other is hydrogen;

each of $R_6$ and $R_7$ represents, independently, hydrogen, $C_1-C_4$ alkyl or fluorine;

m is zero, 1 or 2;

$R_8$ represents $C_1-C_4$ alkyl or a radical chosen from cyclopentyl, cyclohexyl and cycloheptyl, where all the rings are unsubstituted or substituted by one or more substituents chosen from halogen, trihalo-$C_1-C_6$ alkyl, $C_1-C_4$ alkyl and $C_1-C_4$ alkoxy;

and the pharmaceutically or veterinarily acceptable salts thereof.

As stated above this invention covers also the pharmaceutically or veterinarily acceptable salts of the compounds of formula (I).

Preferred salts of the compounds of formula (I) are acid addition salts, with inorganic, e.g. hydrochloric, hydrobromic, hydroiodic, sulphuric, acids or with organic, e.g. acetic, propionic, glycolic, benzoic, citric, tartaric, malonic, malic, maleic, fumaric, cinnamic, mandelic and salicylic, acids or with organic sulphonic acids, e.g. methane sulphonic, p-toluenesulphonic or cyclohexyl-sulphonic acid.

Examples of preferred compounds of the invention are the following:

5c-9α,11α,15(S)-trihydroxy-20-nor-19-cyclohexyl-prost-5-en-13-ynoic acid 2-ethoxy-ethyl ester;

5c-9α,11α,15(S)-trihydroxy-20-nor-19-cyclopentyl-prost-5-en-13-ynoic acid 2-ethoxy-ethyl ester;

5c-9α,11α,15(R)-trihydroxy-16(S)-fluoro-20-nor-19-cyclohexyl-prost-5-en-13-ynoic acid 2-ethoxy-ethyl ester;

5c-9α,11α,15(R,S)-trihydroxy-16(S)-fluoro-20-nor-19-cyclohexyl-prost-5-en-13-ynoic acid 2-ethoxy-ethyl ester;

5c-9α,11α,15(S)-trihydroxy-19,20-dinor-18-cyclohexyl-prost-5-en-13-ynoic acid 2-ethoxy-ethyl ester;

5c-9α,11α,15(S)-trihydroxy-19,20-dinor-18-cyclopentyl-prost-5-en-13-ynoic acid 2-ethoxy-ethyl ester;

5c-9α,11α,15(R)-trihydroxy-16(S)-fluoro-19,20-dinor-18-cyclohexyl-prost-5-en-13-ynoic acid 2-ethoxy-ethyl ester;

5c-9α,11α,15(R,S)-trihydroxy-16(S)-fluoro-19,20-dinor-18-cyclohexyl-prost-5-en-13-ynoic acid 2-ethoxy-ethyl ester;

5c-9α,11α,15(S)-trihydroxy-18,19,20-trinor-17-cyclohexyl-prost-5-en-13-ynoic acid 2-ethoxy-ethyl ester;

5c-9α,11α,15(S)-trihydroxy-18,19,20-trinor-17-cyclopentyl-prost-5-en-13-ynoic acid 2-ethoxy-ethyl ester;

5c-9α,11α,15(R)-trihydroxy-16(S)-fluoro-18,19,20-trinor-17-cyclohexyl-prost-5-en-13-ynoic acid 2-ethoxy-ethyl ester;

5c-9α,11α,15(R,S)-trihydroxy-16(S)-fluoro-18,19,20-trinor-17-cyclohexyl-prost-5-en-13-ynoic acid 2-ethoxy-ethyl ester;

5c-9α,11α,15(R)-trihydroxy-16(S)-fluoro-18,19,20-trinor-17-cyclopentyl-prost-5-en-13-ynoic acid 2-ethoxy-ethyl ester;

5c-9α,11α,15(R,S)-trihydroxy-16(S)fluoro-18,19,20-trinor-17-cyclopentyl-prost-5-en-13-ynoic acid 2-ethoxy-ethyl ester;

5c-9α,11α,15(S)-trihydroxy-17,18,19,20-tetranor-16-cyclohexyl-prost-5-en-13-ynoic acid 2-ethoxy-ethyl ester;

5c-9α,11α,15(S)-trihydroxy-17,18,19,20-tetranor-16-cyclopentyl-prost-5-en-13-ynoic acid 2-ethoxy-ethyl ester;

5c-9α,11α,15(R)-trihydroxy-16(S)-fluoro-17,18,19,20-tetranor-16-cyclohexyl-prost-5-en-13-ynoic acid 2-ethoxy-ethyl ester;

5c-9α,11α,15(R,S)-trihydroxy-16(S)-fluoro-17,18,19,20-tetranor-16-cyclohexyl-prost-5-en-13-ynoic acid 2-ethoxy-ethyl ester;

5c-9α,11α,15(R)-trihydroxy-16(S)-fluoro-16-methyl-18,19,20-trinor-17-cyclohexyl-prost-5-en-13-ynoic acid 2-ethoxy-ethyl ester;

5c-9α,11α,15(R,S)-trihydroxy-16(S)-fluoro-16-methyl-18,19,20-trinor-17-cyclohexyl-prost-5-en-13-ynoic acid 2-ethoxy-ethyl ester;

5c-9α,11α,15(R)-trihydroxy-16(R)-fluoro-16-methyl-18,19,20-trinor-17-cyclohexyl-prost-5-en-13-ynoic acid 2-ethoxy-ethyl ester;

5c-9α,11α,15(S)-trihydroxy-20-nor-19-cyclohexyl-prost-5-en-13-ynoic acid 2-morpholino-ethyl ester;

5c-9α,11α,15(S)-trihydroxy-20-nor-19-cyclopentyl-prost-5-en-13-ynoic acid 2-morpholino-ethyl ester;

5c-9α11α,15(R)-trihydroxy-16(S)-fluoro-20-nor-19-cyclohexyl-prost-5-en-13-ynoic acid 2-morpholino-ethyl ester;

5c-9α,11α,15(R,S)-trihydroxy-16(S)-fluoro-20-nor-19-cyclohexyl-prost-5-en-13-ynoic acid 2-morpholino-ethyl ester;

5c-9α,11α,15(S)-trihydroxy-19,20-dinor-18-cyclohexyl-prost-5-en-13-ynoic acid 2-morpholino-ethyl ester;

5c-9α,11α,15(S)-trihydroxy-19,20-dinor-18-cyclopentyl-prost-5-en-13-ynoic acid 2-morpholino-ethyl ester;

5c-9α,11α,15(R)-trihydroxy-16(S)-fluoro-19,20-dinor-18-cyclohexyl-prost-5-en-13-ynoic acid 2-morpholino-ethyl ester;

5c-9α,11α,15(R,S)-trihydroxy-16(S)-fluoro-19,20-dinor-18-cyclohexyl-prost-5-en-13-ynoic acid 2-morpholino-ethyl ester;

5c-9α,11α,15(S)-trihydroxy-18,19,20-trinor-17-cyclohexyl-prost-5-en-13-ynoic acid 2-morpholino-ethyl ester;

5c-9α,11α,15(S)-trihydroxy-18,19,20-trinor-17-cyclopentyl-prost-5-en-13-ynoic acid 2-morpholino-ethyl ester;

5c-9α,11α,15(R)-trihydroxy-16(S)-fluoro-18,19,20-trinor-17-cyclohexyl-prost-5-en-13-ynoic acid 2-morpholino-ethyl ester;

5c-9α,11α,15(R,S)-trihydroxy-16(S)-fluoro-18,19,20-trinor-17-cyclohexyl-prost-5-en-13-ynoic acid 2-morpholino-ethyl ester;

5c-9α,11α,15(R)-trihydroxy-16(S)-fluoro-18,19,20-trinor-17-cyclopentyl-prost-5-en-13-ynoic acid 2-morpholino-ethyl ester;

5c-9α,11α,15(R,S)-trihydroxy-16(S)fluoro-18,19,20-trinor-17-cyclopentyl-prost-5-en-13-ynoic acid 2-morpholino-ethyl ester;

5c-9α,11α,15(S)-trihydroxy-17,18,19,20-tetranor-16-cyclohexyl-prost-5-en-13-ynoic acid 2-morpholino-ethyl ester;

5c-9α,11α,15(S)-trihydroxy-17,18,19,20-tetranor-16-cyclopentyl-prost-5-en-13-ynoic acid 2-morpholino-ethyl ester;

5c-9α,11α,15(R)-trihydroxy-16(S)-fluoro-17,18,19,20-tetranor-16-cyclohexyl-prost-5-en-13-ynoic acid 2-morpholino-ethyl ester;

5c-9α,11α,15(R,S)-trihydroxy-16(S)-fluoro-17,18,19,20-tetranor-16-cyclohexyl-prost-5-en-13-ynoic acid 2-morpholino-ethyl ester;

5c-9α,11α,15(R)-trihydroxy-16(S)-fluoro-16-methyl-18,19,20-trinor-17-cyclohexyl-prost-5-en-13-ynoic acid 2-morpholino-ethyl ester;

5c-9α,11α,15(R,S)-trihydroxy-16(S)-fluoro-16-methyl-18,19,20-trinor-17-cyclohexyl-prost-5-en-13-ynoic acid 2-morpholino-ethyl ester;

5c-9α,11α,15(R)-trihydroxy-16(R)-fluoro-16-methyl-18,19,20-trinor-17-cyclohexyl-prost-5-en-13-ynoic acid 2-morpholino-ethyl ester;

5c-9α,11α,15(S)-trihydroxy-20-nor-19-cyclohexyl-prost-5-en-13-ynoic acid 2-piperidino-ethyl ester;

5c-9α,11α,15(S)-trihydroxy-20-nor-19-cyclopentyl-prost-5-en-13-ynoic acid 2-piperidino-ethyl ester;

5c-9α,11α,15(R)-trihydroxy-16(S)-fluoro-20-nor-19-cyclohexyl-prost-5-en-13-ynoic acid 2-piperidino-ethyl ester;

5c-9α,11α,15(R,S)-trihydroxy-16(S)-fluoro-20-nor-19-cyclohexyl-prost-5-en-13-ynoic acid 2-piperidino-ethyl ester;

5c-9α,11α,15(S)-trihydroxy-19,20-dinor-18-cyclohexyl-prost-5-en-13-ynoic acid 2-piperidino-ethyl ester;

5c-9α,11α,15(S)-trihydroxy-19,20-dinor-18-cyclopentyl-prost-5-en-13-ynoic acid 2-piperidino-ethyl ester;

5c-9α,11α,15(R)-trihydroxy-16(S)-fluoro-19,20-dinor-18-cyclohexyl-prost-5-en-13-ynoic acid 2-piperidino-ethyl ester;

5c-9α,11α,15(R,S)-trihydroxy-16(S)-fluoro-19,20-dinor-18-cyclohexyl-prost-5-en-13-ynoic acid 2-piperidino-ethyl ester;

5c-9α,11α,15(S)-trihydroxy-18,19,20-trinor-17-cyclohexyl-prost-5-en-13-ynoic acid 2-piperidino-ethyl ester;

5c-9α,11α,15(S)-trihydroxy-18,19,20-trinor-17-cyclopentyl-prost-5-en-13-ynoic acid 2-piperidino-ethyl ester;

5c-9α,11α,15(R)-trihydroxy-16(S)-fluoro-18,19,20-trinor-17-cyclohexyl-prost-5-en-13-ynoic acid 2-piperidino-ethyl ester;

5c-9α,11α,15(R,S)-trihydroxy-16(S)-fluoro-18,19,20-trinor-17-cyclohexyl-prost-5-en-13-ynoic acid 2-piperidino-ethyl ester;

5c-9α,11α,15(R)-trihydroxy-16(S)-fluoro-18,19,20-trinor-17-cyclopentyl-prost-5-en-13-ynoic acid 2-piperidino-ethyl ester;

5c-9α,11α,15(R,S)-trihydroxy-16(S)fluoro-18,19,20-trinor-17-cyclopentyl-prost-5-en-13-ynoic acid 2-piperidino-ethyl ester;

5c-9α,11α,15(S)-trihydroxy-17,18,19,20-tetranor-16-cyclohexyl-prost-5-en-13-ynoic acid 2-piperidino-ethyl ester;

5c-9α,11α,15(S)-trihydroxy-17,18,19,20-tetranor-16-cyclopentyl-prost-5-en-13-ynoic acid 2-piperidino-ethyl ester;

5c-9α,11α,15(R)-trihydroxy-16(S)-fluoro-17,18,19,20-tetranor-16-cyclohexyl-prost-5-en-13-ynoic acid 2-piperidino-ethyl ester;

5c-9α,11α,15(R,S)-trihydroxy-16(S)-fluoro-17,18,19,20-tetranor-16-cyclohexyl-prost-5-en-13-ynoic acid 2-piperidino-ethyl ester;

5c-9α,11α,15(R)-trihydroxy-16(S)-fluoro-16-methyl-18,19,20-trinor-17-cyclohexyl-prost-5-en-13-ynoic acid 2-piperidino-ethyl ester;

5c-9α,11α,15(R,S)-trihydroxy-16(S)-fluoro-16-methyl-18,19,20-trinor-17-cyclohexyl-prost-5-en-13-ynoic acid 2-piperidino-ethyl ester;

5c-9α,11α,15(R)-trihydroxy-16(R)-fluoro-16-methyl-18,19,20-trinor-17-cyclohexyl-prost-5-en-13-ynoic acid 2-piperidino-ethyl ester;

5c-9α,11α,15(S)-trihydroxy-20-nor-19-cyclohexyl-prost-5-en-13-ynoic acid 2-(N,N-dimethylamino)-ethyl ester;

5c-9α,11α,15(S)-trihydroxy-20-nor-19-cyclopentyl-prost-5-en-13-ynoic acid 2-(N,N-dimethylamino)-ethyl ester;

5c-9α,11α,15(R)-trihydroxy-16(S)-fluoro-20-nor-19-cyclohexyl-prost-5-en-13-ynoic acid 2-(N,N-dimethylamino)-ethyl ester;

5c-9α,11α,15(R,S)-trihydroxy-16(S)-fluoro-20-nor-19-cyclohexyl-prost-5-en-13-ynoic acid 2-(N,N-dimethylamino)-ethyl ester 5c-9α,11α,15(S)-trihydroxy-19,20-dinor-18-cyclohexyl-prost-5-en-13-ynoic acid 2-(N,N-dimethylamino)-ethyl ester;

5c-9α,11α,15(S)-trihydroxy-19,20-dinor-18-cyclopentyl-prost-5-en-13-ynoic acid 2-(N,N-dimethylamino)-ethyl ester;

5c-9α,11α,15(R)-trihydroxy-16(S)-fluoro-19,20-dinor-18-cyclohexyl-prost-5-en-13-ynoic acid 2-(N,N-dimethylamino)-ethyl ester 5c-9α,11α,15(R,S)-trihydroxy-16(S)-fluoro-19,20-dinor-18-cyclohexyl-prost-5-en-13-ynoic acid 2-(N,N-dimethylamino)-ethyl ester 5c-9α,11α,15(S)-trihydroxy-18,19,20-trinor-17-cyclohexyl-prost-5-en-13-ynoic acid 2-(N,N-dimethylamino)-ethyl ester;

5c-9α,11α,15(S)-trihydroxy-18,19,20-trinor-17-cyclopentyl-prost-5-en-13-ynoic acid 2-(N,N-dimethylamino)-ethyl ester;

5c-9α,11α,15(R)-trihydroxy-16(S)-fluoro-18,19,20-trinor-17-cyclohexyl-prost-5-en-13-ynoic acid 2-(N,N-dimethylamino)-ethyl ester 5c-9α,11α,15(R,S)-trihydroxy-16(S)-fluoro-18,19,20-trinor-17-cyclohexyl-prost-5-en-13-ynoic acid 2-(N,N-dimethylamino)-ethyl ester 5c-9α,11α,15(R)-trihydroxy-16(S)-fluoro-18,19,20-trinor-17-cyclopentyl-prost-5-en-13-ynoic acid 2-(N,N-dimethylamino)-ethyl ester;

5c-9α,11α,15(R,S)-trihydroxy-16(S)fluoro-18,19,20-trinor-17-cyclopentyl-prost-5-en-13-ynoic acid 2-(N,N-dimethylamino)-ethyl ester 5c-9α,11α,15(S)-trihydroxy-17,18,19,20-tetranor-16-cyclohexyl-prost-5-en-13-ynoic acid 2-(N,N-dimethylamino)-ethyl ester;

5c-9α,11α,15(S)-trihydroxy-17,18,19,20-tetranor-16-cyclopentyl-prost-5-en-13-ynoic acid 2-(N,N-dimethylamino)-ethyl ester;

5c-9α,11α,15(R)-trihydroxy-16(S)-fluoro-17,18,19,20-tetranor-16-cyclohexyl-prost-5-en-13-ynoic acid 2-(N,N-dimethylamino)-ethyl ester 5c-9α,11α,15(R,S)-trihydroxy-16(S)-fluoro-17,18,19,20-tetranor-16-cyclohexyl-prost-5-en-13-ynoic acid 2-(N,N-dimethylamino)-ethyl ester;

5c-9α,11α,15(R)-trihydroxy-16(S)-fluoro-16-methyl-18,19,20-trinor-17-cyclohexyl-prost-5-en-13-ynoic acid 2-(N,N-dimethylamino)-ethyl ester;

5c-9α,11α,15(R,S)-trihydroxy-16(S)-fluoro-16-methyl-18,19,20-trinor-17-cyclohexyl-prost-5-en-13-ynoic acid 2-(N,N-dimethylamino)-ethyl ester;

5c-9α,11α,15(R)-trihydroxy-16(R)-fluoro-16-methyl-18,19,20-trinor-17-cyclohexyl-prost-5-en-13-ynoic acid 2-(N,N-dimethylamino)-ethyl ester;

5c-9-oxo-11α,15(S)-dihydroxy-20-nor-19-cyclohexyl-prost-5-en-13-ynoic acid 2-ethoxy-ethyl ester;

5c-9-oxo-11α,15(S)-dihydroxy-20-nor-19-cyclopentyl-prost-5-en-13-ynoic acid 2-ethoxy-ethyl ester;

5c-9-oxo-11α,15(R)-dihydroxy-16(S)-fluoro-20-nor-19-cyclohexyl-prost-5-en-13-ynoic acid 2-ethoxy-ethyl ester;

5c-9-oxo-11α,15(R,S)-dihydroxy-16(S)-fluoro-20-nor-19-cyclohexyl-prost-5-en-13-ynoic acid 2-ethoxy-ethyl ester;

5c-9-oxo-11α,15(S)-dihydroxy-19,20-dinor-18-cyclohexyl-prost-5-en-13-ynoic acid 2-ethoxy-ethyl ester;

5c-9-oxo-11α,15(S)-dihydroxy-19,20-dinor-18-cyclopentyl-prost-5-en-13-ynoic acid 2-ethoxy-ethyl ester;

5c-9-oxo-11α,15(R)-dihydroxy-16(S)-fluoro-19,20-dinor-18-cyclohexyl-prost-5-en-13-ynoic acid 2-ethoxy-ethyl ester;

5c-9-oxo-11α,15(R,S)-dihydroxy-16(S)-fluoro-19,20-dinor-18-cyclohexyl-prost-5-en-13-ynoic acid 2-ethoxy-ethyl ester;

5c-9-oxo-11α,15(S)-dihydroxy-18,19,20-trinor-17-cyclohexyl-prost-5-en-13-ynoic acid 2-ethoxy-ethyl ester;

5c-9-oxo-11α,15(S)-dihydroxy-18,19,20-trinor-17-cyclopentyl-prost-5-en-13-ynoic acid 2-ethoxy-ethyl ester;

5c-9-oxo-11α,15(R)-dihydroxy-16(S)-fluoro-18,19,20-trinor-17-cyclohexyl-prost-5-en-13-ynoic acid 2-ethoxy-ethyl ester;

5c-9-oxo-11α,15(R,S)-dihydroxy-16(S)-fluoro-18,19,20-trinor-17-cyclohexyl-prost-5-en-13-ynoic acid 2-ethoxy-ethyl ester;

5c-9-oxo-11α,15(R)-dihydroxy-16(S)-fluoro-18,19,20-trinor-17-cyclopentyl-prost-5-en-13-ynoic acid 2-ethoxy-ethyl ester;

5c-9-oxo-11α,15(R,S)-dihydroxy-16(S)-fluoro-18,19,20-trinor-17-cyclopentyl-prost-5-en-13-ynoic acid 2-ethoxy-ethyl ester;

5c-9-oxo-11α,15(S)-dihydroxy-17,18,19,20-tetranor-16-cyclohexyl-prost-5-en-13-ynoic acid 2-ethoxy-ethyl ester;

5c-9-oxo-11α,15(S)-dihydroxy-17,18,19,20-tetranor-16-cyclopentyl-prost-5-en-13-ynoic acid 2-ethoxy-ethyl ester;

5c-9-oxo-11α,15(R)-dihydroxy-16(S)-fluoro-17,18,19,20-tetranor-16-cyclohexyl-prost-5-en-13-ynoic acid 2-ethoxy-ethyl ester;

5c-9-oxo-11α,15(R,S)-dihydroxy-16(S)-fluoro-17,18,19,20-tetranor-16-cyclohexyl-prost-5-en-13-ynoic acid 2-ethoxy-ethyl ester;

5c-9-oxo-11α,15(R)-dihydroxy-16(S)-fluoro-16-methyl-18,19,20-trinor-17-cyclohexyl-prost-5-en-13-ynoic acid 2-ethoxy-ethyl ester;

5c-9-oxo-11α,15(R,S)-dihydroxy-16(S)-fluoro-16-methyl-18,19,20-trinor-17-cyclohexyl-prost-5-en-13-ynoic acid 2-ethoxy-ethyl ester; and 5c-9-oxo-11α,15(R)-dihydroxy-16(R)-fluoro-16-methyl-18,19,20-trinor-17-cyclohexyl-prost-5-en-13-ynoic acid 2-ethoxy-ethyl ester; and the pharmaceutically or veterinarily acceptable salts of the hereabove listed 2-(N,N-dimethylamino)-ethyl esters.

The compounds of general formula (I) can be prepared by a process comprising:

(a) reacting an optically active or racemic compound of formula (II) or a reactive derivative thereof

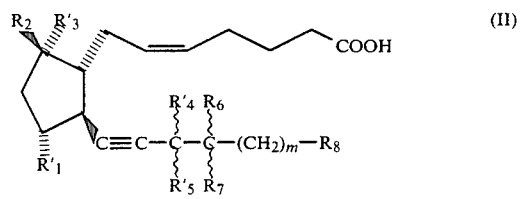

wherein when the symbol ≅ represents a double bond, $R'_1$ is hydrogen and $R_2$ and $R'_3$, taken together, form an oxo group; or, when the symbol ≅ represents a single bond, $R'_1$ is hydroxy or a known protecting group bound to the ring through an ethereal oxygen atom, $R_2$ is hydrogen and $R'_3$ is hydroxy, acyloxy or a known protecting group bound to the ring through an ethereal oxygen atom or $R_2$ and $R'_3$, taken together, form an oxo group; one of $R'_4$ and $R'_5$ is hydroxy or a known protecting group bound to the chain through an ethereal oxygen atom and the other is hydrogen; and $R_6$, $R_7$, m and $R_8$ are as defined above, with a compound of formula (III)

H—R   (III)

wherein R is as defined above, thus giving an optically active or racemic compound of formula (IV)

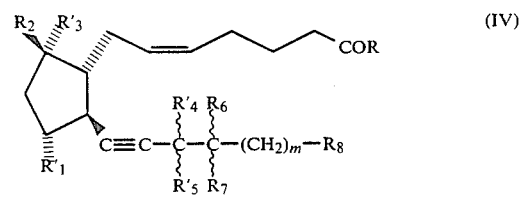

wherein R, $R'_3$, $R_2$, $R'_1$, $R'_4$, $R'_5$, $R_6$, $R_7$, m, $R_8$ and the symbol ≅ are as defined above, and then, when necessary, removing the hydroxy protecting groups; or (b) reacting a compound of formula (V), in optically active or racemic form,

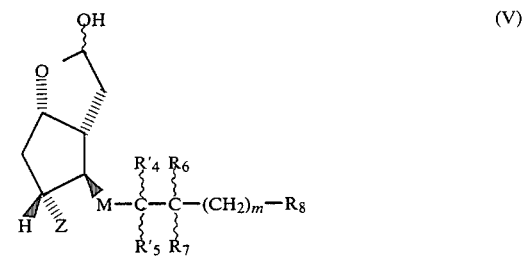

wherein M is —C≡C— or

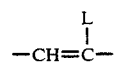

and L is bromine, chlorine or iodine; Z is hydroxy or a known protecting group bound to the ring through an ethereal oxygen atom; and $R'_4$, $R'_5$, $R_6$, $R_7$, m and $R_8$ are as defined above, with a Wittig reagent containing a —(CH$_2$)$_4$—COR group, wherein R is as defined above, to give an optically active or racemic compound of formula (VI)

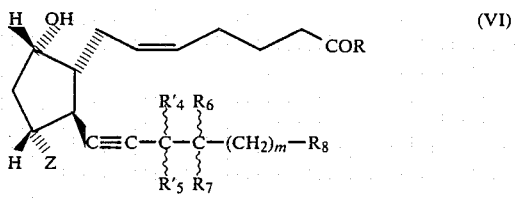

wherein R, Z, R'$_4$, R'$_5$, R$_6$, R$_7$, m and R$_8$ are as defined above, which, when the 11- and 15-hydroxy groups are in the protected form, if desired, may be esterified to give a 9α-acyloxy derivative of a compound of formula (VI), and then removing the protecting groups at the 11- and/or 15-positions, if present, both in a compound of formula (VI) and in its acyloxy derivatives, thus giving a compound of formula (I), wherein R$_3$ is hydroxy or acyloxy, R$_2$ is hydrogen, R$_1$ is hydroxy, the symbol ⸺ represents a single bond and R, R$_4$, R$_5$, R$_6$, R$_7$, m and R$_8$ are as defined above; or (c) oxidizing an optically active or racemic compound of formula (VII)

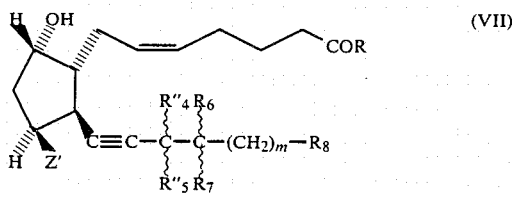

wherein Z' is a known protecting group bound to the ring through an ethereal oxygen atom; one of R''$_4$ and R''$_5$ is hydrogen and the other is a known protecting group bound to the chain through an ethereal oxygen atom; and R, R$_6$, R$_7$, m and R$_8$ are as defined above; to give an optically active or racemic compound of formula (VIII)

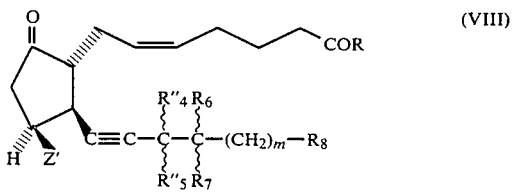

wherein Z', R, R''$_4$, R''$_5$, R$_6$, R$_7$, m, and R$_8$ are as defined above, and removing the protecting groups in a compound of formula (VIII) to give, depending on the reaction conditions, either a compound of formula (I), where the symbol ⸺ represents a single bond, R$_1$ is hydroxy, R$_2$ and R$_3$, taken together, form an oxo group and R, R$_4$, R$_5$, R$_6$, R$_7$, m and R$_8$ are as defined above, or a compound of formula (I), where the symbol represents a double bond, R$_1$ is hydrogen, R$_2$ and R$_3$, taken together form an oxo group and R, R$_4$, R$_5$, R$_6$, R$_7$, m and R$_8$ are as defined above and/or, if desired, reacting a compound of formula (I), wherein the hydroxy group(s) are, optionally, protected, with an acid or a reactive derivative thereof, followed, if required, by removal of the protecting group(s), to give a salt of a compound of formula (I); or obtaining a compound of formula (I) in free form from a salt thereof; and/or if desired converting a compound of formula (I) or a salt thereof into another compound of formula (I) or a salt thereof, and/or if desired, resolving a mixture of isomers into the single isomers.

A known protecting group bound to the ring or to the chain through an ethereal oxygen atom, i.e. an ether group, should be easily convertible to a hydroxy group under mild reaction conditions, e.g. acid hydrolysis. Examples are acetalic ethers, enol ethers and silyl ethers.

The preferred groups are:

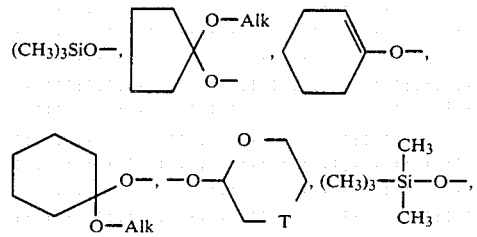

wherein T is —O— or —CH$_2$— and Alk represents a lower alkyl group.

An amino protecting group may be for example a protecting group usually employed in the chemistry of peptides. Examples of amino protecting groups are formyl, an optional halo-substituted C$_2$-C$_6$ aliphatic acyl, preferably chloroacetyl, dichloroacetyl, tert-butoxycarbonyl, p-nitro-benzyloxy-carbonyl or trityl.

Also the amino protecting groups are then removed at the end of the reaction, usually in a known way. For example when the amino protecting group is the monochloroacetyl group, it may be removed by treatment with thiourea; the formyl and the trifluoroacetyl groups may be removed by treatment with potassium carbonate in aqueous methanol and the trityl group by treatment with formic or trifluoroacetic acid.

A reactive derivative of a compound of formula (II), may be for example, an acyl halide, an azide, a reactive ester or a salt, such as, the salt formed with alkaline or alkaline-earth metals or an organic base.

The reaction between a compound of formula (II) or a reactive derivative thereof and a compound of formula (III) may be performed either at room temperature or under cooling, in a suitable solvent, such as, dioxane, tetrahydrofuran, benzene, toluene, chloroform, methylene chloride, dimethyl formamide and, if desired, in the presence of a base, e.g. sodium bicarbonate, potassium bicarbonate, sodium carbonate or in the presence of another acid acceptor, such as an anionic exchange resin.

When a compound of formula (II) is reacted with a compound of formula (III), the reaction may be conveniently performed in the presence of a condensing agent, e.g. a carbodiimide, carbonyldiimidazole and similar.

In particular, the reaction between an acid of formula (II) and a compound of formula (III), where R represents —Y—(CH$_2$)$_n$—Z, that is a compound of formula H—Y—(CH$_2$)$_n$—Z, wherein Y, n and Z are as defined above, may be carried out in the presence of a suitable dehydrating agent, which, as stated above, may be a carbodiimide, in particular, of formula R$^{IV}$—N=C-

=N—$R^V$, wherein each of $R^{IV}$ and $R^V$, being the same or different, represents an alkyl or cycloalkyl radical, e.g. ethyl, 3-dimethylaminopropyl, isopropyl or cyclohexyl. This reaction may be carried out in an inert solvent, for example, chosen from $CH_2Cl_2$, $CHCl_3$, ethyl ether, tetrahydrofuran, dimethylformamide, benzene, toluene or a suitable hydrocarbon, like pentane, hexane and, if desired, in the presence of a suitable acylation catalyst, e.g. pyridine, 4-dimethylaminopyridine (DMAP).

The reaction is conveniently made in two steps in which the first step is the preparation of the substituted isourea derivative of formula (IX).

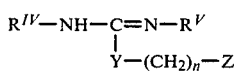
(IX)

wherein $R^{IV}$, $R^V$, Y, n and Z are as defined above, and the second step in the reaction of this compound with a suitable prostanoic acid of formula (II).

The reaction between an alkyl ester of an acid of formula (II) and ammonia to give a compound of formula (I), wherein R is

wherein R' and R" are both hydrogen, may be carried out with gaseous ammonia in a lower aliphatic alcohol, e.g., methanol; in general when the same alkyl ester is reacted with a suitable amine of formula (III) the reaction may be carried out in an inert solvent, e.g. benzene or toluene, methanol, ethanol, diethylether, tetrahydrofuran and dimethylformamide, and at temperatures ranging from the room temperature to the reflux temperature.

The reaction between an acyl halide, e.g. the chloride, of an acid of formula (II) and an amine of formula (III) may be carried out in an inert solvent, e.g., benzene or toluene, or in an aqueous solvent in the presence of an inorganic base, e.g. $NaHCO_3$ or $Na_2CO_3$, as acid acceptor.

When in the lactol of formula (V) M is —C≡C— or —CH∇Cl—, in which L is bromine or iodine, the Wittig reaction may be carried out by using about 1 up to 4 moles, preferably 2, of Wittig reagent per mole of lactol and the reaction may last from about 10–20 minutes to several hours, depending on the temperature, on the concentration of the reacting mixture and on the Wittig reagent used.

When, in the lactol of formula (V), M is —CH=CL—, wherein L is chlorine, it is necessary, by using, for example, 1.5 to 2.5 moles of Wittig reagent per mole of lactol, to prolong the reaction time up to ten hours, or, if it is desired to use shorter reaction times, it is necessary to employ a great excess of Wittig reagent: at least 5 moles of Wittig reagent per mole of lactol, for reaction times of about 30 minutes. Therefore, when in the lactol of formula (V) M is —CH=CL—, L is preferably bromine or iodine.

When in the lactol of formula (V) M is —CH=CL—, wherein L is bromine, chlorine or iodine, the hydrogen atom linked to the carbon atom in the 14-position may be either in the trans-position, i.e. geometric trans-isomers, or in the cis-position, i.e. geometric cis-isomers.

Preferably they are in the trans-position. The Wittig reaction is performed by using the conditions usually followed for this kind of reaction, i.e. in an organic solvent, for example diethylether, hexane, dimethylsulphoxide, tetrahydrofuran, dimethylformamide or hexamethylphosphoramide in the presence of a base, preferably sodium hydride and potassium tert.butoxide, at temperatures from about 0° C. to the reflux temperature of the reaction mixture, preferably at room temperature or below. The term "Wittig reagent" includes compounds of general formula $(Q)_3P^\oplus$—$(CH_2)_4$—COR Hal$^\ominus$, where Q represents aryl, e.g. phenyl, or alkyl, e.g. ethyl; Hal represents halogen, e.g. bromine or chlorine, and R is as defined above.

The preparation of the Wittig reagent is discussed in detail by Trippett, Quart. Rev.: (1963) XVII, No 4,406. When in the lactol of formula (V) M is —CH=CL—, wherein L is as defined above, during the reaction with the Wittig reagent, the dehydrohalogenation takes place, as easily when the hydrogen atom linked to the carbon atom in the 13-position and the halogen atom linked to the carbon atom in the 14-position are in the trans-position as when they are in the cis-position.

The optional acylation of the 9α-hydroxy group in a compound of formula (VI) to afford the respective 9α-acyloxy derivative may be performed in conventional way, for example, by treatment with an anhydride or a halide, e.g. a chloride of a carboxylic acid in the presence of a base.

The oxidation of the 9α-hydroxy group in a compound of formula (VII) to yield the respective 9-oxo derivative may be carried out through, for example, Jones reagent (G.I. Poos and al. Am. Soc. 75, 422, 1953) or Moffat reagent (Am. Soc. 87, 5661, 1965).

The removal of the known protecting groups bound to the ring or, respectively, to the chain by an ethereal oxygen atom is, whenever required, performed under conditions of mild acid hydrolysis, for example with a mono- or poly-carboxylic acid, e.g. formic, acetic, oxalic, citric and tartaric acid, and in a solvent, which may be, for example, water, acetone, tetrahydrofuran, dimethoxyethane and lower aliphatic alcohols and mixture of them or with a sulphonic acid, e.g. p-toluene-sulphonic acid in a solvent, such as, a lower aliphatic alcohol, e.g. in methanol or in ethanol or with a polystyrene sulphonic resin. For example a solution of 0.1 to 0.25N poly-carboxylic acid, in water e.g. oxalic or citric acid, is used in the presence of a suitable low boiling co-solvent which is miscible with water and which can be easily removed in vacuo at the end of the reaction. As discussed previously, removal of the protecting groups in a compound of formula (VIII) may give, depending on the conditions, either a compound of formula (I) where the symbol    is a single bond, $R_1$ is hydroxy and $R_2$ and $R_3$, taken together, from a oxo group, or a compound of formula (I), where the symbol    is a double bond, $R_2$ is hydrogen and $R_2$ and $R_3$, taken together, form an oxo group.

The first may be prepared as the sole reaction product by running the reaction between 25° C. and 35°–40° C., while at higher temperatures, for instance for several hours at reflux, only the second is obtained.

The optional salification of a compound of formula (I) as well as the conversion of a salt into a free compound and the separation of a mixture of isomers into the single isomers may be carried out by conventional methods. For example the separation of a mixture of geometric isomers, e.g. cis- and trans-isomers, may be carried out by fractional crystallization from a suitable solvent or by chromatography: either column chromatography or high pressure liquid chromatography. Compounds of formula (II) and (V) are already known (for example, some of them are described in British Patent specifications No. 1.483.880 and No. 1.583.263) or may be obtained from known compounds by known processes. For example, lactol (V), wherein M is —C≡C— may be prepared by dehydrohalogenation of a lactol (V), in which M is —CH=CL—, where L is halogen. Dehydrohalogenation may be carried out in an aprotic solvent, preferably chosen from dimethylsulphoxide, dimethylformamide and hexamethylphosphoramide, by treatment with a base preferably chosen from potassium tert-butylate, an alkali metal amide and the $CH_3SO_2—CH_2^\ominus$ anion.

Also the compounds of formula (III) are known or may be prepared by known methods from known compounds.

Among the reaction intermediates described above, the compound of formula (IV) is new and is another object of the present invention.

The compounds of the invention are useful in human therapy and in veterinary medicine in all the diseases in which natural prostaglandins are required, but with the advantages of a superior resistance to the enzyme 15-prostaglandin dehydrogenase, which as known, rapidly inactivates the natural prostaglandins. In addition, the compounds of the invention, for example 5c-9α,1-1α,15(S)-trihydroxy-20-nor-19-cyclohexyl-prost-5-en-13-ynoic acid ethoxy-ethyl ester and 5c-9α,11α,15(S)-trihydroxy-17,18,19,20-tetranor-16-cyclohexyl-prost-5-en-13-ynoic acid 2-ethoxy-ethyl ester, when administered orally, show a more lasting activity than the parent acid or alkyl ester derivatives.

The compounds of the invention, besides being endowed with more lasting activity when administered orally, show a more lasting and greater activity than the natural prostaglandins also when administered parenterally, e.g. by intravenous or intramuscular injection, vaginally or by inhalation.

This difference is due to the fact that the compounds of this invention are both more resistant to metabolic inactivations and more efficiently adsorbed by the epithelial tissues than the respective acid analogues.

In relation to the enhanced absorption related to their reduced polarity and enhanced hydrophilicity, the compounds of the invention are subjected to an initial rapid tissue distribution and then they are slowly released back into the blood, where they are hydrolyzed to free acids, thus obtaining a higher blood levels of active prostanoids. Experiments in vitro confirm the extremely rapid plasmatic hydrolysis of the ester and amide derivatives of the invention to give the respective acid derivatives.

The toxicity of the compounds of the invention was found to be quite negligible and therefore they may be safely used both in therapy and in veterinary medicine. The evaluation of the toxicity (as orientative acute toxicity, i.e. $LD_{50}$) was carried out, e.g., as follows: nine hours food deprived mice were treated orally with single administration of increasing doses, then housed and normally fed; the $LD_{50}$ was assessed on the seventh day after the treatment.

For example the $LD_{50}$ of the compound 5c-9α,1-1α,15(S)-trihydroxy-20-nor-19-cyclohexyl-prost-5-en-13-ynoic acid 2-ethoxy-ethyl ester was found >3 g/kg body weight.

As already said, the compounds covered by this invention may be used in the same applications where natural prostaglandins are required. For example, these compounds and in particular the 9α-hydroxy derivatives exhibit oxytocic action, that is, they may be used in the place of oxytocin to induce labor or to expel a dead fetus in pregnant females, both in humans and in animals.

In this application, the compounds are administered either by intravenous infusion at a dose of approximately 0.01–0.05 μg/kg/minute until the end of labor, or by mouth at a single or multiple doses from about 0.05 mg to about 5 mg pro dose. Further, the compounds covered by this invention, particularly the 9α-hydroxy derivatives, are also endowed with luteolytic activity and are more potent, in particular when administered parenterally, than the related well known compounds mentioned above. For example, the luteolytic activity of the compound 5c-9α,11α,15(S)-trihydroxy-18,19,20-trinor-17-cyclohexyl-prost-5-en-13-ynoic acid 2-ethoxy-ethyl ester, expressed as $ED_{50}$ value and evaluated in the hamster after subcutaneous injection [according to A. B. LABHSETWAR, Nature, vol. 230, page 528 (1971)], was found to be 5 μg/kg, while, in the same experimental conditions, the $ED_{50}$ value for the well known compound 5c-9α,11α,15(S)-trihydroxy-18,19,20-trinor-17-cyclohexyl-prost-5-en-13-ynoic acid methyl ester was found to be 9 μg/kg. The compounds of the invention may therefore be used in fertility control with the advantage of a considerably reduced capacity to stimulate the smooth muscles; thus the side effects of natural prostaglandins, like vomiting and diarrhea, are absent.

Another useful pharmacological property of the compounds of this invention, particularly the 9-oxo derivatives, is their anti-ulcerogenic activity. In fact, they are useful to reduce and control excessive gastric secretion in mammals and so reduce or eliminate the formation of gastroin-testinal ulcers and accelerate the healing process of any ulcers already present in the gastrointestinal tract. In this connexion the compounds of the invention are also useful for reducing the undesirable gastrointestinal side-effects resulting from systemic administration of antiinflammatory prostaglandin synthetase inhibitors and may be, therefore, used for this purpose in association with them. In this applications the compounds of the invention are administered, preferably, by oral route in a single or multiple doses, where the dose for adult humans varies from about 0.1 μg to about 50 μg/kg body weight.

In all the above applications the exact treatment level depends on the case history of the patient being treated and the specific treatment level along the guidelines given above is left to the discretion of the therapist.

The compounds of formula (IV) are endowed with the same pharmacologic activities of the compounds of formula (I) and are administered to humans or animals for the same therapeutic purposes, at the same dosage levels and through the same routes of administration.

The pharmaceutical compositions of the invention are usually prepared following conventional methods and are administered in a pharmaceutically suitable form. For example, the solid oral forms may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinyl pyrrolidone; disaggregating agents, e.g. a starch, alginic acid, alginates, sodium starch glycolate; effervescing mixtures; dyestuffs; sweeteners; wetting agents, for instance, leci-thin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, such as, sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

As stated above a further way of administration may be inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquefied propellant, such as; dichlorodifluoromethane or dichlorotetrafluoroethane, to be administered from a pressurized container, i.e., an aerosol dispenser.

When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin. Other suitable pharmaceutical form may be for example powders. The powders may be administered by means of a suitable insufflator device and in this case the fine particle sized powders of the active ingredient may be mixed with a diluent material such a lactose.

This invention is illustrated but not limited by the following examples.

The abbreviations THP, DMSO, THF and EtOH refer to tetrahydropyranyl, dimethylsulphoxide, tetrahydrofuran and ethyl alcohol, respectively.

All the temperatures are expressed in degrees centigrade, and optical rotation measures refer to 20° C. and a concentration of 1% by weight of the compound in the specific solvent.

EXAMPLE 1

A solution of 5c-9α,11α,15(R)-trihydroxy-16(S)-fluoro-20-methyl-prost-5-en-13-ynoic acid methyl ester (0.5 g) in 10 ml of methyl alcohol was cooled with ice-bath; dry $NH_3$ was bubbled into the solution until saturation. The reaction vessel was closed and maintained at room temperature for 24 hours, then the $NH_3$ was stripped with $N_2$ and alcohol removed. The crude product was purified on silica gel by using a mixture of hexane/ethylacetate as eluent and 0.45 g of pure 5c-9α,11α,15(R)-trihydroxy-16(S)-fluoro-20-methyl-prost-5-en-13-ynoic acid amide were collected: $[\alpha]_D = +15.5$; $[\alpha]_{365} = +60.7$ (C=1 EtOH).

By proceeding analogously the following compounds were obtained:

5c-9α,11α,15(S)-trihydroxy-16(R)-fluoro-20-ethyl-prost-5-en-13-ynoic acid amide; $[\alpha]_D = +29.6$ 5c-9α,11α,15(R,S)-trihydroxy-16(S)-fluoro-20-ethyl-prost-5-en-13-ynoic acid amide; $[\alpha]_D = +20.8$ 5c-9α,11α,15(R)-trihydroxy-16(S)-fluoro-20-methyl-prost-5-en-13-ynoic acid amide; $[\alpha]_D = +22.7$ 5c-9α,11α,15(R,S)-trihydroxy-16(S)-fluoro-20-methyl-prost-5-en-13-ynoic acid amide; $[\alpha]_D = +21.2$ 5c-9α,11α,15(S)-trihydroxy-16(R)-fluoro-20-methyl-prost-5en-13-ynoic acid amide; $[\alpha]_D = +32.1$ 5c-9α,11α,15(R)-trihydroxy-16(S)-fluoro-16-methyl-17,18,19,20-tetranor-prost-5-en-13-ynoic acid amide; $[\alpha]_D = +27$ 5c-9α,11α,15(R)-trihydroxy-16(S)-fluoro-16,20-dimethyl-prost-5-en-13-ynoic acid amide; $[\alpha]_D = +28.2$ 5c-9α,11α,15(R,S)-trihydroxy-16(S)-fluoro-16-methyl-17,18,19,20-tetranor-prost-5-en-13-ynoic acid amide; $[\alpha]_D = +30.6$ 5c-9α,11α,15(R,S)-trihydroxy-16(S)-fluoro-16,20-dimethyl-prost-5-en-13-ynoic acid amide; $[\alpha]_D = +31.3$ 5c-9α,11α,15(R)-trihydroxy-16(S)-fluoro-16-methyl-20-ethyl-prost-5-en-13-ynoic acid amide; $[\alpha]_D = +36$.

EXAMPLE 2

A solution of 1.162 g of potassium tert.butoxide in 10 ml of dry DMSO was stirred under dry nitrogen and 4.3 g of triphenylphosphonium pentanoic acid 2-piperidino-ethyl ester bromide were added. During the addition the temperature of the reacting mixture was kept below 30° C. through water bath; then a solution of 0.830 g of 3α,5α,dihydroxy-2β-[2-bromo-3(S)-hydroxy-5-cyclohexyl-pent-trans-1-enyl]-1α-cyclopentane acetaldehyde-α-lactol-bis-THP-ether in 10 ml of dry DMSO was added. The reaction was completed in about 30 minutes and the mixture was quenched with water and then extracted with diethyl ether. The solvent was removed and the crude product was purified on silica gel by using a mixture of hexane/ethyl acetate=6/4 as eluent thus obtaining 0.810 g of pure 5c-9α,1-1α,15(S)-trihydroxy-18,19,20-trinor-17-cyclohexyl-prost-5-en-13-ynoic acid 2-piperidino-ethyl ester 11,15-bis-THP-ether: $[\alpha]_D = +61,7$ (C=1 EtOH).

Starting from the suitable triphenylphosphonium derivatives and bis-THP-ether lactols, the 2-ethoxy-ethyl esters 11,15-bis-THP-ether, the 2-piperidino-ethyl esters, 11,15-bis-THP-ether, the 2-morpholino-ethyl esters 11,15-bis-THP-ether and the 2-(N,N-dimethylamino)-ethyl esters 11,15-bis-THP-ether of the following acids were obtained:

5c-9α,11α,15(S)-trihydroxy-20-nor-19-cyclohexyl-prost-5-en-13-ynoic acid;

5c-9α,11α,15(S)-trihydroxy-20-nor-19-cyclopentyl-prost-5-en-13-ynoic acid;

5c-9α,11α,15(R)-trihydroxy-16(S)-fluoro-20-nor-19-cyclohexyl-prost-5en-13-ynoic acid;

5c-9α,11α,15(R,S)-trihydroxy-16(S)-fluoro-20-nor-19-cyclohexyl-prost-5-en-13-ynoic acid;

5c-9α,11α,15(S)-trihydroxy-19,20-dinor-18-cyclohexyl-prost-5-en-13-ynoic acid;

5c-9α,11α,15(S)-trihydroxy-19,20-dinor-18-cyclopentyl-prost-5-en-13-ynoic acid;

5c-9α,11α,15(R)-trihydroxy-16(S)-fluoro-19,20-dinor-18-cyclohexyl-prost-5en-13-ynoic acid;

5c-9α,11α,15(R,S)-trihydroxy-16(S)-fluoro-19,20-dinor-18-cyclohexyl-prost-5-en-13-ynoic acid;

5c-9α,11α,15(S)-trihydroxy-18,19,20-trinor-17-cyclohexyl-prost-5-en-13-ynoic acid;

5c-9α,11α,15(S)-trihydroxy-18,19,20-trinor-17-cyclopentyl-prost-5-en-13-ynoic acid;

5c-9α,11α,15(R)-trihydroxy-16(S)-fluoro-18,19,20-trinor-17-cyclohexyl-prost-5-en-13-ynoic acid;

5c-9α,11α,15(R,S)-trihydroxy-16(S)-fluoro-18,19,20-trinor-17-cyclohexyl-prost-5-en-13-ynoic acid;

5c-9α,11α,15(R)-trihydroxy-16(S)-fluoro-18,19,20-trinor-17-cyclopentyl-prost-5-en-13-ynoic acid;

5c-9α,11α,15(R,S)-trihydroxy-16(S)fluoro-18,19,20-trinor-17-cyclopentyl-prost-5-en-13-ynoic acid;

5c-9α,11α,15(S)-trihydroxy-17,18,19,20-tetranor-16-cyclohexyl-prost-5-en-13-ynoic acid;

5c-9α,11α,15(S)-trihydroxy-17,18,19,20-tetranor-16-cyclopentyl-prost-5en-13-ynoic acid;

5c-9α,11α,15(R)-trihydroxy-16(S)-fluoro-17,18,19,20-tetranor-16-cyclohexyl-prost-5-en-13-ynoic acid;

5c-9α,11α,15(R,S)-trihydroxy-16(S)-fluoro-17,18,19,20-tetranor-16-cyclohexyl-prost-5-en-13-ynoic acid;

5c-9α,11α,15(R)-trihydroxy-16(S)-fluoro-16-methyl-18,19,20-trinor-17-cyclohexyl-prost-5-en-13-ynoic acid;

5c-9α,11α,15(R,S)-trihydroxy-16(S)-fluoro-16-methyl-18,19,20-trinor-17-cyclohexyl-prost-5-en-13-ynoic acid; and 5c-9α,11α,15(R)-trihydroxy-16(R)-fluoro-16-methyl-18,19,20-trinor-17-cyclohexyl-prost-5-en-13-ynoic acid.

5c-9α,11α,15(S)-trihydroxy-18,19,20-trinor-17-cyclohexyl-prost-5-en-13-ynoic acid 2-(piperidino)-ethyl ester 11,15-bis THP-ether (0.810 g) was dissolved in a mixture of acetone (10 ml) and 1N oxalic acid (10 ml) and stirred 6 hours at 40° C. The reaction solution was diluted with 10 ml of water. The acetone was distilled and the mixture extracted with ethyl ether. The crude product was purified on silica gel using ethyl acetate:cyclohexane=50:50 as eluent, thus affording 0.535 g of pure 5c-9α,11α,15(S)-trihydroxy-18,19,20-trinor-17-cyclohexyl-prost-5-en-13-ynoic acid 2-(piperidino)-ethyl ester $[\alpha]_D= +22.7$ (C=1 EtOH).

By proceeding analogously the 2-ethoxy-ethyl esters, 2-piperidino-ethyl esters, 2-morpholino-ethyl esters and 2-(N,N-dimethylamino)ethyl esters of the hereinbefore listed acids were obtained.

EXAMPLE 3

1.7 ml of Jones reagent were dropped into a solution of 1.27 g of 5c-9α,11α,15(S)-trihydroxy-18,19,20-trinor-17-cyclohexyl-prost-5-en-13-ynoic acid 2-(N,N-dimethylamino)ethyl amide 11,15-bis-THP-ether in 20 ml of acetone cooled at −25° C. and by keeping the temperature at −25° C. When the addition was completed the temperature of the reacting mixture was allowed to rise to −8° C. and the mixture was stirred for 20 minutes.

This was then diluted with benzene, washed with saturated $(NH_4)_2SO_4$ aqueous solution until neutral, then dried and evaporated at 20° C. under vacuum.

The crude residue (1.2 g) containing 5c-9-oxo-11α,15(S)-dihydroxy-18,19,20-trinor-17-cyclohexyl-prost-5-en-13-ynoic acid, 2-(N,N-dimethylamino)-ethyl amide 11,15-bis-THP-ether, was dissolved in 30 ml of acetone and treated with 5.7 ml of 1N oxalic acid solution at 40° C. for 8 hours.

After the reaction was completed, the acetone was evaporated under vacuum to give a residue which after chromatography on silica gel using a mixture of ethyl acetate/hexane=30/70 afforded 0.650 g of pure 5c-9-oxo-11α,15(S)-dihydroxy-18,19,20-trinor-17-cyclohexyl-prost-5-en-13-ynoic acid, 2-(N,N-dimethylamino)-ethyl amide: $[\alpha]_D= -27.8$ (C=1 EtOH).

By proceeding analogously starting from the 2-ethoxy-ethyl esters 11,15-bis-THP-ether, 2-morpholino-ethyl esters 11,15-bis-THP-ether, the 2-piperidino-ethyl esters 11,15-bis-THP-ether and the 2-(N,N-dimethylamino)-ethyl esters 11,15-bis-THP-ether reported in Example 2, the following compounds were obtained:

5c-9-oxo-11α,15(S)-dihydroxy-20-nor-19-cyclohexyl-prost-5-en-13-ynoic acid 2-ethoxy-ethyl ester; $[\alpha]_D= -31.2$ 5c-9-oxo-11α,15(S)-dihydroxy-20-nor-19-cyclopentyl-prost-5-en-13-ynoic acid 2-ethoxy-ethyl ester; $[\alpha]_D= -32.1$ 5c-9-oxo-11α,15(R)-dihydroxy-16(S)-fluoro-20-nor-19-cyclohexyl-prost-5-en-13-ynoic acid 2-ethoxy-ethyl ester; $[\alpha]_D= -29.6$ 5c-9-oxo-11α,15(R,S)-dihydroxy-16(S)-fluoro-20-nor-19-cyclohexyl-prost-5-en-13-ynoic acid 2-ethoxy-ethyl ester; $[\alpha]_D= -33.5$ 5c-9-oxo-11α,15(S)-dihydroxy-19,20-dinor-18-cyclohexyl-prost-5-en-13-ynoic acid 2-ethoxy-ethyl ester; $[\alpha]_D= -32.1$ 5c-9-oxo-11α,15(S)-dihydroxy-19,20-dinor-18-cyclopentyl-prost-5-en-13-ynoic acid 2-ethoxy-ethyl ester; $[\alpha]_D= -37.8$ 5c-9-oxo-11α,15(R)-dihydroxy-16(S)-fluoro-19,20-dinor-18-cyclohexyl-prost-5-en-13-ynoic acid 2-ethoxy-ethyl ester; $[\alpha]_D= -34.9$ 5c-9-oxo-11α,15(R,S)-dihydroxy-16(S)-fluoro-19,20-dinor-18-cyclohexyl-prost-5-en-13-ynoic acid 2-ethoxy-ethyl ester; $[\alpha]_D= -33.8$ 5c-9-oxo-11α,15(S)-dihydroxy-18,19,20-trinor-17-cyclohexyl-prost-5-en-13-ynoic acid 2-ethoxy-ethyl ester; $[\alpha]_D= -38.7$ 5c-9-oxo-11α,15(S)-dihydroxy-18,19,20-trinor-17-cyclopentyl-prost-5-en-13-ynoic acid 2-ethoxy-ethyl ester; $[\alpha]_D= -40.2$ 5c-9-oxo-11α,15(R)-dihydroxy-16(S)-fluoro-18,19,20-trinor-17-cyclohexyl-prost-5-en-13-ynoic acid 2-ethoxy-ethyl ester; $[\alpha]_D= -18.2$ 5c-9-oxo-11α,15(R,S)-dihydroxy-16(S)-fluoro-18,19,20-trinor-17-cyclohexyl-prost-5-en-13-ynoic acid 2-ethoxy-ethyl ester; $[\alpha]_D= -27.7$ 5c-9-oxo-11α,15(R)-dihydroxy-16(S)-fluoro-18,19,20-trinor-17-cyclopentyl-prost-5-en-13-ynoic acid 2-ethoxy-ethyl ester; $[\alpha]_D= -31.6$ 5c-9-oxo-11α,15(R,S)-dihydroxy-16(S)-fluoro-18,19,20-trinor-17-cyclopentyl-prost-5-en-13-ynoic acid 2-ethoxy-ethyl ester; $[\alpha]_D= -29.7$ 5c-9-oxo-11α,15(S)-dihydroxy-17,18,19,20-tetranor-16-cyclohexyl-prost-5-en-13-ynoic acid 2-ethoxy-ethyl ester; $[\alpha]_D = -41.2$ 5c-9-oxo-11α,15(S)-dihydroxy-17,18,19,20-tetranor-16-cyclo-pentyl-prost-5-en-13-ynoic acid 2-ethoxy-ethyl ester; $[\alpha]_D = -48.6$ 5c-9-oxo-11α,15(R)-dihydroxy-16(S)-fluoro-17,18,19,20-tetranor-16-cyclohexyl-prost-5-en-13-ynoic acid 2-ethoxy-ethyl ester; $[\alpha]_D = -21.7$ 5c-9-oxo-11α,15(R,S)-dihydroxy-16(S)-fluoro-17,18,19,20-tetranor-16-cyclohexyl-prost-5-en-13-ynoic acid 2-ethoxy-ethyl ester; $[\alpha]_D = -20.2$ 5c-9-oxo-11α,15(R)-dihydroxy-16(S)-fluoro-16-methyl-18,19,20-trinor-17-cyclohexyl-prost-5-en-13-ynoic acid 2-ethoxy-ethyl ester; $[\alpha]_D = -48.5$ 5c-9-oxo-11α,15(R,S)-dihydroxy-16(S)-fluoro-16-methyl-18,19,20-trinor-17-cyclohexyl-prost-5-en-13-ynoic acid 2-ethoxy-ethyl ester; $[\alpha]_D = -45.5$ 5c-9-oxo-11α,15(R)-dihydroxy-16(R)-fluoro-16-methyl-18,19,20-trinor-17-cyclohexyl-prost-5-en-13-ynoic acid 2-ethoxy-ethyl ester; $[\alpha]_D = -56.3$ 5c-9-oxo-11α,15(S)-dihydroxy-20-nor-19-cyclohexyl-prost-5-en-13-ynoic acid 2-piperidino-ethyl ester; $[\alpha]_D = -30.7$ 5c-9-oxo-11α,15(S)-dihydroxy-20-nor-19-cyclopentyl-prost-5-en-13-ynoic acid 2-piperidino-ethyl ester; $[\alpha]_D = -29.8$ 5c-9-oxo-11α,15(R)-dihydroxy-16(S)-fluoro-20-nor-19-cyclohexyl-prost-5-en-13-ynoic acid 2-piperidino-ethyl ester; $[\alpha]_D = -30.1$ 5c-9-oxo-11α,15(R,S)-dihydroxy-16(S)-fluoro-20-nor-19-cyclohexyl-prost-5-en-13-ynoic acid 2-piperidino-ethyl ester; $[\alpha]_D = -31.5$ 5c-9-oxo-11α,15(S)-dihydroxy-19,20-dinor-18-cyclohexyl-prost-5-en-13-ynoic acid 2-piperidino-ethyl ester; $[\alpha]_D = -30.2$ 5c-9-oxo-11α,15(S)-dihydroxy-19,20-dinor-18-cyclopentyl-prost-5-en-13-ynoic acid 2-piperidino-ethyl ester; $[\alpha]_D = -32.5$ 5c-9-oxo-11α,15(R)-dihydroxy-16(S)-fluoro-19,20-dinor-18-cyclohexyl-prost-5-en-13-ynoic acid 2-piperidino-ethyl ester; $[\alpha]_D = -31.7$ 5c-9-oxo-11α,15(R,S)-dihydroxy-16(S)-fluoro-19,20-dinor-18-cyclohexyl-prost-5-en-13-ynoic acid 2-piperidino-ethyl ester; $[\alpha]_D = -32.5$ 5c-9-oxo-11α,15(S)-dihydroxy-18,19,20-trinor-17-cyclohexyl-prost-5-en-13-ynoic acid 2-piperidino-ethyl ester; $[\alpha]_D = -32.9$ 5c-9-oxo-11α,15(S)-dihydroxy-18,19,20-trinor-17-cyclopentyl-prost-5-en-13-ynoic acid 2-piperidino-ethyl ester; $[\alpha]_D = -35.2$ 5c-9-oxo-11α,15(R)-dihydroxy-16(S)-fluoro-18,19,20-trinor-17-cyclohexyl-prost-5-en-13-ynoic acid 2-piperidino-ethyl ester; $[\alpha]_D = -20.1$ 5c-9-oxo-11α,15(R,S)-dihydroxy-16(S)-fluoro-18,19,20-trinor-17-cyclohexyl-prost-5-en-13-ynoic acid 2-piperidino-ethyl ester; $[\alpha]_D = -22.5$ 5c-9-oxo-11α,15(R)-dihydroxy-16(S)-fluoro-18,19,20-trinor-17-cyclopentyl-prost-5-en-13-ynoic acid 2-piperidino-ethyl ester; $[\alpha]_D = -30.2$ 5c-9-oxo-11α,15(R,S)-dihydroxy-16(S)-fluoro-18,19,20-trinor-17-cyclopentyl-prost-5-en-13-ynoic acid 2-piperidino-ethyl ester; $[\alpha]_D = -27.5$ 5c-9-oxo-11α,15(S)-dihydroxy-17,18,19,20-tetranor-16-cyclohexyl-prost-5-en-13-ynoic acid 2-piperidino-ethyl ester; $[\alpha]_D = -40.7$ 5c-9-oxo-11α,15(S)-dihydroxy-17,18,19,20-tetranor-16-cyclopentyl-prost-5-en-13-ynoic acid 2-piperidino-ethyl ester; $[\alpha]_D = -45.5$ 5c-9-oxo-11α,15(R)-dihydroxy-16(S)-fluoro-17,18,19,20-tetranor-16-cyclohexyl-prost-5-en-13-ynoic acid 2-piperidino-ethyl-ester; $[\alpha]_D = -20$ 5c-9-oxo-11α,15(R,S)-dihydroxy-16(S)-fluoro-17,18,19,20-tetranor-16-cyclohexyl-prost-5-en-13-ynoic acid 2-piperidino-ethyl ester; $[\alpha]_D = -20.1$ 5c-9-oxo-11α,15(R)-dihydroxy-16(S)-fluoro-16-methyl-18,19,20-trinor-17-cyclohexyl-prost-5-en-13-ynoic acid 2-piperidino-ethyl ester; $[\alpha]_D = -42.9$ 5c-9-oxo-11α,15(R,S)-dihydroxy-16(S)-fluoro-16-methyl-18,19,20-trinor-17-cyclohexyl-prost-5-en-13-ynoic acid 2-piperidino-ethyl ester; $[\alpha]_D = -41.7$ 5c-9-oxo-11α,15(R)-dihydroxy-16(R)-fluoro-16-methyl-18,19,20-trinor-17-cyclohexyl-prost-5-en-13-ynoic acid 2-piperidino-ethyl ester; $[\alpha]_D = -55.6$ 5c-9-oxo-11α,15(S)-dihydroxy-20-nor-19-cyclohexyl-prost-5-en-13-ynoic acid 2-morpholino-ethyl ester; $[\alpha]_D = -30.7$ 5-c-9-oxo-11α,15(S)-dihydroxy-20-nor-19-cyclopentyl-prost-5-en-13-ynoic acid 2-morpholino-ethyl ester; $[\alpha]_D = -31$ 5c-9-oxo-11α,15(R)-dihydroxy-16(S)-fluoro-20-nor-19-cyclohexyl-prost-5-en-13-ynoic acid 2-morpholino-ethyl ester; $[\alpha]_D = -28.9$ 5c-9-oxo-11α,15(R,S)-dihydroxy-16(S)-dihydroxy-16(S)-fluoro-20-nor-19-cyclohexyl-prost-5-en-13-ynoic acid 2-morpholino-ethyl ester; $[\alpha]_D = -32.9$ 5c-9-oxo-11α,15(S)-dihydroxy-19,20-dinor-18-cyclohexylprost-5-en-13-ynoic acid 2-morpholino-ethyl ester; $[\alpha]_D = -31.9$ 5c-9-oxo-11α,15(S)-dihydroxy-19,20-dinor-18-cyclopentyl-prost-5-en-13-ynoic acid 2-morpholino-ethyl ester; $[\alpha]_D = -35.8$ 5c-9-oxo-11α,15(R)-dihydroxy-16(S)-fluoro-19,20-dinor-18-cyclohexyl-prost-5-en-13-ynoic acid 2-morpholino-ethyl ester; $[\alpha]_D = -33.7$ 5c-9-oxo-11α,15(R,S)-dihydroxy-16(S)-fluoro-19,20-dinor-18-cyclohexyl-prost-5-en-13-ynoic acid 2-morpholino-ethyl ester; $[\alpha]_D = -30.6$ 5c-9-oxo-11α,15(S)-dihydroxy-18,19,20-trinor-17-cyclohexyl-prost-5-en-13-ynoic acid 2-morpholino-ethyl ester; $[\alpha]_D = -36.2$ 5c-9-oxo-11α,15(S)-dihydroxy-18,19,20-trinor-17-cyclopentyl-prost-5-en-13-ynoic acid 2-morpholino-ethyl ester; $[\alpha]_D = -39.1$ 5c-9-oxo-11α,15(R)-dihydroxy-16(S)-fluoro-18,19,20-trinor-17-cyclohexyl-prost-5-en-13-ynoic acid 2-morpholino-ethyl ester; $[\alpha]_D = -21.1$ 5c-9-oxo-11α,15(R,S)-dihydroxy-16(S)-fluoro-18,19,20-trinor-17-cyclohexyl-prost-5-en-13-ynoic acid 2-morpholino-ethyl ester; $[\alpha]_D = -26.6$ 5c-9-oxo-11α,15(R)-dihydroxy-16(S)-fluoro-18,19,20-trinor-17-cyclopentyl-prost-5-en-13-ynoic acid 2-morpholino-ethyl ester; $[\alpha]_D = -30.2$ 5c-9-oxo-11α,15(R,S)-dihydroxy-16(S)-fluoro-18,19,20-trinor-17-cyclopentyl-prost-5-en-13-ynoic acid 2-morpholino-ethyl ester; $[\alpha]_D = -25.9$ 5c-9-oxo-11α,15(S)-dihydroxy-17,18,19,20-tetranor-16-cyclohexyl-prost-5-en-13-ynoic acid 2-morpholino-ethyl ester; $[\alpha]_D = -40.2$ 5c-9-oxo-11α,15(S)-dihydroxy-17,18,19,20-tetranor-16-cyclopentyl-prost-5-en-13-ynoic acid 2-morpholino-ethyl ester; $[\alpha]_D = -45$ 5c-9-oxo-11α,15(R)-dihydroxy-16(S)-fluoro-17,18,19,20-tetranor-16-cyclohexyl-prost-5-en-13-ynoic acid 2-morpholino-ethyl ester; $[\alpha]_D = -20.1$ 5c-9-oxo-11α,15(R,S)-dihydroxy-16(S)-fluoro-17,1,19,20-tetranor-16-cyclohexyl-prost-5-en-13-ynoic acid 2-morpholino-ethyl ester; $[\alpha]_D = -20.7$ 5c-9-oxo-11α,15(R)-dihydroxy-16(S)-fluoro-16-methyl-18,19,20-trinor-17-cyclohexyl-prost-5-en-13-ynoic acid 2-morpholino-ethyl ester; $[\alpha]_D = -49.2$ 5c-9-oxo-11α,15(R,S)-dihydroxy-16(S)-fluoro-16-methyl-18,19,20-trinor-17-cyclohexyl-prost-5-en-13-ynoic acid 2-morpholino-ethyl ester; $[\alpha]_D = -46$ 5c-9-oxo-11α,15(R)-dihydroxy-16(R)-fluoro-16-methyl-18,19,20-trinor-17-cyclohexyl-prost-5-en-13-ynoic acid 2-morpholino-ethyl ester; $[\alpha]_D = -49.8$ 5c-9-oxo-11α,15(S)-dihydroxy-20-nor-19-cyclohexyl-prost-5-en-13-ynoic acid 2-(N,N-dimethylamino)-ethyl ester; $[\alpha]_D = -32.4$ 5c-9-oxo-11α,15(S)-dihydroxy-20-nor-19-cyclopentyl-prost-5-en-13-ynoic acid 2-(N,N-dimethylamino)-ethyl ester; $[\alpha]_D = -33.3$ 5c-9-oxo-11α,15(R)-dihydroxy-16(S)-fluoro-20-nor-19-cyclohexyl-prost-5-en-B 13-ynoic acid 2-(N,N-dimethylamino)-ethyl ester; $[\alpha]_D = -31.6$ 5c-9-oxo-11α,15(R,S)-dihydroxy-16(S)-fluoro-20-nor-19-cyclohexyl-prost-5-en-13-ynoic acid 2-(N,N-dimethylamino)-ethyl ester; $[\alpha]_D = -32.1$ 5c-9-oxo-11α,15(S)-dihydroxy-19,20-dinor-18-cyclohexyl-prost-5-en-13-ynoic acid 2-(N,N-dimethylamino)-ethyl ester; $[\alpha]_D = -31$ 5c-9-oxo-11α,15(S)-dihydroxy-19,20-dinor-18-cyclopentyl-prost-5-en-13-ynoic acid 2-(N,N-dimethylamino)-ethyl ester; $[\alpha]_D = -36.5$ 5c-9-oxo-11α,15(R)-dihydroxy-16(S)-fluoro-19,20-dinor-18-cyclohexyl-prost-5-en-13-ynoic acid 2-(N,N-dimethylamino)-ethyl ester; $[\alpha]_D = -30.7$ 5c-9-oxo-11α,15(R,S)-dihydroxy-16(S)-fluoro-19,20-dinor-18-cyclohexyl-prost-5-en-13-ynoic acid 2-(N,N-dimethylamino)-ethyl ester; $[\alpha]_D = -31.9$ 5c-9-oxo-11α,15(S)-dihydroxy-18,19,20-trinor-17-cyclohexyl-prost-5-en-13-ynoic acid 2-(N,N-dimethylamino)-ethyl ester; $[\alpha]_D = -42.5$ 5c-9-oxo-11α,15(S)-dihydroxy-18,19,20-trinor-17-cyclopentyl-prost-5-en-13-ynoic acid 2-(N,N-dimethylamino)-ethyl ester; $[\alpha]_D = -48.9$ 5c-9-oxo-11α,15(R)-dihydroxy-16(S)-fluoro-18,19,20-trinor-17-cyclohexyl-prost-5-en-13-ynoic acid 2-(N,N-dimethylamino)-ethyl ester; $[\alpha]_D = -27.2$ 5c-9-oxo-11α,15(R,S)-dihydroxy-16(S)-fluoro-18,19,20-trinor-17-cyclohexyl-prost-5-en-13-ynoic acid 2-(N,N-dimethylamino)-ethyl ester; $[\alpha]_D = -29.2$ 5c-9-oxo-11α,15(R)-dihydroxy-16(S)-fluoro-18,19,20-trinor-17-cyclopentyl-prost-5-en-13-ynoic acid 2-(N,N-dimethylamino)-ethyl ester; $[\alpha]_D = -30.7$ 5c-9-oxo-11α15(R,S)-dihydroxy-16(S)-fluoro-18,19,20-trinor-17-cyclopentyl-prost-5-en-13-ynoic acid 2-(N,N-dimethylamino)-ethyl ester; $[\alpha]_D = -25.2$ 5c-9-oxo-11α,15(S)-dihydroxy-17,18,19,20-tetranor-16-cyclohexyl-prost-5-en-13-ynoic acid 2-(N,N-dimethylamino)-ethyl ester; $[\alpha]_D = -40.8$ 5c-9-oxo-11α,15(S)-dihydroxy-17,18,19,20-tetranor-16-cyclopentyl-prost-5-en-13-ynoic acid 2-(N,N-dimethylamino)-ethyl ester; $[\alpha]_D = -50.2$ 5c-9-oxo-11α,15(R)-dihydroxy-16(S)-fluoro-17,18,19,20-tetranor-16-cyclohexyl-prost-5-en-13-ynoic acid 2-(N,N-dimethylamino)-ethyl ester; $[\alpha]_D = -19.6$ 5c-9-oxo-11α,15(R,S)-dihydroxy-16(S)-fluoro-17,18,19,20-tetranor-16-cyclohexyl-prost-5-en-13-ynoic acid 2-(N,N-dimethylamino)-ethyl ester; $[\alpha]_D = -22.2$ 5c-9-oxo-11α,15(R)-dihydroxy-16(S)-fluoro-16-methyl-18,19,20-trinor-17-cyclohexyl-prost-5-en-13-ynoic acid 2-(N,N-dimethylamino)-ethyl ester; $[\alpha]_D = -39.7$ 5c-9-oxo-11α,15(R,S)-dihydroxy-16(S)-fluoro-16-methyl-18,19,20-trinor-17-cyclohexyl-prost-5-en-13-ynoic acid 2-(N,N-dimethylamino)-ethyl ester; $[\alpha]_D = -40.9$ 5c-9-oxo-11α,15(R)-dihydroxy-16(R)-fluoro-16-methyl-18,19,20-trinor-17-cyclohexyl-prost-5-en-13-ynoic acid 2-(N,N-dimethylamino)-ethyl ester; $[\alpha]_D = -51.3$

EXAMPLE 4

Under nitrogen atmosphere 1.49 g of NaH (80% in mineral oil) suspension in dry DMSO (40 ml) was heated at 60° C. for 3 hours until hydrogen liberation has stopped, then the solution was cooled to 10°÷15° C. and a solution of triphenyl-(4-morpholino-2-ethoxycarbonylbutyl)-phosphonium bromide (13.63 g) in 20 ml of dry DMSO was added under vigorous stirring.

3α,5α-dihydroxy-2β-[2-bromo-3(S,R)-hydroxy-4(S)-fluoro-5-cyclohexyl-pent-trans-1-enyl]-1α-cyclopentane acetaldehyde-γ-lactol (1.1 g) was added to the resulting deep red solution. After the solution was completed, the obtained mixture was diluted with a mixture of ice/water=1/1 and then extracted with diethyl ether. The solvent was removed and the crude product was purified on silica gel by using a mixture of ethyl acetate/hexane=80:20 as eluent: 0.975 g of pure 5c-9α,11α,15(R,S)-trihydroxy-16(S)-fluoro-18,19,20-trinor-17-cyclohexyl-prost-5-en-13-ynoic acid 2-morpholino-ethyl ester were obtained: $[\alpha]_D = +26.3$ (C=1 EtOH).

By proceeding analogously the following compounds were obtained:

5c-9α,11α,15(S)-trihydroxy-20-nor-19-cyclohexyl-prost-5-en-13-ynoic acid 2-morpholino-ethyl ester; $[\alpha]_D = +20.1$ 5c-9α,11α,15(S)-trihydroxy-20-nor-19-cyclopentyl-prost-5-en-13-ynoic acid 2-morpholino-ethyl ester; $[\alpha]_D = +26.4$ 5c-9α,11α,15(R)-trihydroxy-16(S)-fluoro-20-nor-19-cyclohexyl-prost-5-en-13-ynoic acid 2-morpholino-ethyl ester; $[\alpha]_D = +29.5$ 5c-9α,11α,15(R,S)-trihydroxy-16(S)-fluoro-20-nor-19-cyclohexyl-prost-5-en-13-ynoic acid 2-morpholino-ethyl ester, $[\alpha]_D = +26.2$ 5c-9α,11α,15(S)-trihydroxy-19,20-dinor-18-cyclohexyl-prost-5-en-13-ynoic acid 2-morpholino-ethyl ester; $[\alpha]_D = +30.7$ 5c-9α,11α,15(S)-trihydroxy-19,20-dinor-18-cyclopentyl-prost-5-en-13-ynoic acid 2-morpholino-ethyl ester; $[\alpha]_D = +33.2$ 5c-9α,11α,15(R)-trihydroxy-16(S)-fluoro-19,20-dinor-18-cyclohexyl-prost-5-en-13-ynoic acid 2-morpholino-ethyl ester; $[\alpha]_D = +18.7$ 5c-9α,11α,15(R,S)-trihydroxy-16(S)-fluoro-19,20-dinor-18-cyclohexyl-prost-5-en-13-ynoic acid 2-morpholino-ethyl ester; $[\alpha]_D = +20$ 5c-9α,11α,15(S)-trihydroxy-18,19,20-trinor-17-cyclohexyl-prost-5-en-13-ynoic acid 2-morpholino-ethyl ester; $[\alpha]_D = +17.6$ 5c-9α,11α,15(S)-trihydroxy-18,19,20-trinor-17-cyclopentyl-prost-5-en-13-ynoic acid 2-morpholino-ethyl ester; [α]$_D$=+19.6

5c-9α,11α,15(R)-trihydroxy-16(S)-fluoro-18,19,20-trinor-17-cyclohexyl-prost-5-en-13-ynoic acid 2-morpholino-ethyl ester; [α]$_D$=+13.1

5c-9α,11α,15(R,S)-trihydroxy-16(S)-fluoro-18,19,20-trinor-17-cyclohexyl-prost-5-en-13-ynoic acid 2-morpholino-ethyl ester; [α]$_D$=+16.8

5c-9α,11α,15(R)-trihydroxy-16(S)-fluoro-18,19,20-trinor-17-cyclopentyl-prost-5-en-13-ynoic acid 2-morpholino-ethyl ester; [α]$_D$=+13.9

5c-9α,11α,15(R,S)-trihydroxy-16(S)fluoro-18,19,20-trinor-17-cyclopentyl-prost-5-en-13-ynoic acid 2-morpholino-ethyl ester; [α]$_D$=+21.7

5c-9α,11α,15(S)-trihydroxy-17,18,19,20-tetranor-16-cyclohexyl-prost-5-en-13-ynoic acid 2-morpholino-ethyl ester; [α]$_D$=+37.9

5c-9α,11α,15(S)-trihydroxy-17,18,19,20-tetranor-16-cyclopentyl-prost-5-en-13-ynoic acid 2-morpholino-ethyl ester; [α]$_D$=+42.2

5c-9α,11α,15(R)-trihydroxy-16(S)-fluoro-17,18,19,20-tetranor-16-cyclohexyl-prost-5-en-13-ynoic acid 2-morpholino-ethyl ester; [α]$_D$=+14.1

5c-9α,11α,15(R,S)-trihydroxy-16(S)-fluoro-17,18,19,20-tetranor-16-cyclohexyl-prost-5-en-13-ynoic acid 2-morpholino-ethyl ester; [α]$_D$=+20.5

5c-9α,11α,15(R)-trihydroxy-16(S)-fluoro-16-methyl-18,19,20-trinor-17-cyclohexyl-prost-5-en-13-ynoic acid 2-morpholino-ethyl ester; [α]$_D$=+33.1

5c-9α,11α,15(R,S)-trihydroxy-16(S)-fluoro-16-methyl-18,19,20-trinor-17-cyclohexyl-prost-5-en-13-ynoic acid 2-morpholino-ethyl ester; [α]$_D$=+37.6

5c-9α,11α,15(R)-trihydroxy-16(R)-fluoro-16-methyl-18,19,20-trinor-17-cyclohexyl-prost-5-en-13-ynoic acid 2-morpholino-ethyl ester; [α]$_D$=+44.4

5c-9α,11α,15(S)-trihydroxy-20-nor-19-cyclohexyl-prost-5-en-13-ynoic acid 2-ethoxy-ethyl ester;

5c-9α,11α,15(S)-trihydroxy-20-nor-19-cyclopentyl-prost-5-en-13-ynoic acid 2-ethoxy-ethyl ester;

5c-9α,11α,15(R)-trihydroxy-16(S)-fluoro-20-nor-19-cyclohexyl-prost-5-en-13-ynoic acid 2-ethoxy-ethyl ester;

5c-9α,11α,15(R,S)-trihydroxy-16(S)-fluoro-20-nor-19-cyclohexyl-prost-5-en-13-ynoic acid 2-ethoxy-ethyl ester;

5c-9α,11α,15(S)-trihydroxy-19,20-dinor-18-cyclohexyl-prost-5-en-13-ynoic acid 2-ethoxy-ethyl ester;

5c-9α,11α,15(S)-trihydroxy-19,20-dinor-18-cyclopentyl-prost-5-en-13-ynoic acid 2-ethoxy-ethyl ester;

5c-9α,11α,15(R)-trihydroxy-16(S)-fluoro-19,20-dinor-18-cyclohexyl-prost-5-en-13-ynoic acid 2-ethoxy-ethyl ester;

5c-9α,11α,15(R,S)-trihydroxy-16(S)-fluoro-19,20-dinor-18-cyclohexyl-prost-5-en-13-ynoic acid 2-ethoxy-ethyl ester;

5c-9α,11α,15(S)-trihydroxy-18,19,20-trinor-17-cyclohexyl-prost-5-en-13-ynoic acid 2-ethoxy-ethyl ester;

5c-9α,11α,15(S)-trihydroxy-18,19,20-trinor-17-cyclopentyl-prost-5-en-13-ynoic acid 2-ethoxy-ethyl ester;

5c-9α,11α,15(R)-trihydroxy-16(S)-fluoro-18,19,20-trinor-17-cyclohexyl-prost-5-en-13-ynoic acid 2-ethoxy-ethyl ester;

5c-9α,11α,15(R,S)-trihydroxy-16(S)-fluoro-18,19,20-trinor-17-cyclohexyl-prost-5-en-13-ynoic acid 2-ethoxy-ethyl ester;

5c-9α,11α,15(R)-trihydroxy-16(S)-fluoro-18,19,20-trinor-17-cyclopentyl-prost-5-en-13-ynoic acid 2ethoxy-ethyl ester;

5c-9α,11α,15(R,S)-trihydroxy-16(S)fluoro-18,19,20-trinor-17-cyclopentyl-prost-5-en-13-ynoic acid 2-ethoxy-ethyl ester;

5c-9α,11α,15(S)-trihydroxy-17,18,19,20-tetranor-16-cyclohexyl-prost-5-en-13-ynoic acid 2-ethoxy-ethyl ester;

5c-9α,11α,15(S)-trihydroxy-17,18,19,20-tetranor-16-cyclopentyl-prost-5-en-13-ynoic acid 2-ethoxy-ethyl ester;

5c-9α,11α,15(R)-trihydroxy-16(S)-fluoro-17,18,19,20-tetranor-16-cyclohexyl-prost-5-en-13-ynoic acid 2-ethoxy-ethyl ester;

5c-9α,11α,15(R,S)-trihydroxy-16(S)-fluoro-17,18,19,20-tetranor-16-cyclohexyl-prost-5-en-13-ynoic acid 2-ethoxy-ethyl ester;

5c-9α,11α,15(R)-trihydroxy-16(S)-fluoro-16-methyl-18,19,20-trinor-17-cyclohexyl-prost-5-en-13-ynoic acid 2-ethoxy-ethyl ester;

5c-9α,11α,15(R,S)-trihydroxy-16(S)-fluoro-16-methyl-18,19,20-trinor-17-cyclohexyl-prost-5-en-13-ynoic acid 2-ethoxy-ethyl ester;

5c-9α,11α,15(R)-trihydroxy-16(R)-fluoro-16-methyl-18,19,20-trinor-17-cyclohexyl-prost-5-en-13-ynoic acid 2-ethoxy-ethyl ester;

5c-9α,11α,15(S)-trihydroxy-20-nor-19-cyclohexyl-prost-5-en-13-ynoic acid 2-piperidino-ethyl ester;

5c-9α,11α,15(S)-trihydroxy-20-nor-19-cyclopentyl-prost-5-en-13-ynoic acid 2-piperidino-ethyl ester;

5c-9α,11α,15(R)-trihydroxy-16(S)-fluoro-20-nor-19-cyclohexyl-prost-5-en-13-ynoic acid 2-piperidino-ethyl ester;

5c-9α,11α,15(R,S)-trihydroxy-16(S)-fluoro-20-nor-19-cyclohexyl-prost-5-en-13-ynoic acid 2-piperidino-ethyl ester;

5c-9α,11α,15(S)-trihydroxy-19,20-dinor-18-cyclohexyl-prost-5-en-13-ynoic acid 2-piperidino-ethyl ester;

5c-9α,11α,15(S)-trihydroxy-19,20-dinor-18-cyclopentyl-prost-5-en-13-ynoic acid 2-piperidino-ethyl ester;

5c-9α,11α,15(R)-trihydroxy-16(S)-fluoro-19,20-dinor-18-cyclohexyl-prost-5-en-13-ynoic acid 2-piperidino-ethyl ester;

5c-9α,11α,15(R,S)-trihydroxy-16(S)-fluoro-19,20-dinor-18-cyclohexyl-prost-5-en-13-ynoic acid 2-piperidino-ethyl ester;

5c-9α,11α,15(S)-trihydroxy-18,19,20-trinor-17-cyclohexyl-prost-5-en-13-ynoic acid 2-piperidino-ethyl ester;

5c-9α,11α,15(S)-trihydroxy-18,19,20-trinor-17-cyclopentyl-prost-5-en-13-ynoic acid 2-piperidino-ethyl ester;

5c-9α,11α,15(R)-trihydroxy-16(S)-fluoro-18,19,20-trinor-17-cyclohexyl-prost-5-en-13-ynoic acid 2-piperidino-ethyl ester;

5c-9α,11α,15(R,S)-trihydroxy-16(S)-fluoro-18,19,20-trinor-17-cyclohexyl-prost-5-en-13-ynoic acid 2-piperidino-ethyl ester;

5c-9α,11α,15(R)-trihydroxy-16(S)-fluoro-18,19,20-trinor-17-cyclopentyl-prost-5-en-13-ynoic acid 2-piperidino-ethyl ester;

5c-9α,11α,15(R,S)-trihydroxy-16(S)-fluoro-18,19,20-trinor-17-cyclopentyl-prost-5-en-13-ynoic acid 2-piperidino-ethyl ester 5c-9α,11α,15(S)-trihydroxy-17,18,19,20-tetranor-16-cyclohexyl-prost-5-en-13-ynoic acid 2-piperidino-ethyl ester;

5c-9α,11α,15(S)-trihydroxy-17,18,19,20-tetranor-16-cyclopentyl-prost-5-en-13-ynoic acid 2-piperidino-ethyl ester;

5c-9α,11α,15(R)-trihydroxy-16(S)-fluoro-17,18,19,20-tetranor-16-cyclohexyl-prost-5-en-13-ynoic acid 2-piperidino-ethyl ester;

5c-9α,11α,15(R,S)-trihydroxy-16(S)-fluoro-17,18,19,20-tetranor-16-cyclohexyl-prost-5-en-13-ynoic acid 2-piperidino-ethyl ester;

5c-9α,11α,15(R)-trihydroxy-16(S)-fluoro-16-methyl-18,19,20-trinor-17-cyclohexyl-prost-5en-13-ynoic acid 2-piperidino-ethyl ester;

5c-9α,11α,15(R,S)-trihydroxy-16(S)-fluoro-16-methyl-18,19,20-trinor-17-cyclohexyl-prost-5-en-13-ynoic acid 2-piperidino-ethyl ester;

5c-9α,11α,15(R)-trihydroxy-16(R)-fluoro-16-methyl-18,19,20-trinor-17-cyclohexyl-prost-5-en-13-ynoic acid 2-piperidino-ethyl ester;

5c-9α,11α,15(S)-trihydroxy-20-nor-19-cyclohexyl-prost-5-en-13-ynoic acid 2-(N,N-dimethylamino)-ethyl ester;

5c-9α,11α,15(S)-trihydroxy-20-nor-19-cyclopentyl-prost-5-en-13-ynoic acid 2-(N,N-dimethylamino)-ethyl ester;

5c-9α,11α,15(R)-trihydroxy-16(S)-fluoro-20-nor-19-cyclohexyl-prost-5-en-13-ynoic acid 2-(N,N-dimethylamino)-ethyl ester;

5c-9α,11α,15(R,S)-trihydroxy-16(S)-fluoro-20-nor-19-cyclohexyl-prost-5-en-13-ynoic acid 2-(N,N-dimethylamino)-ethyl ester 5c-9α,11α,15(S)-trihydroxy-19,20-dinor-18-cyclohexyl-prost-5-en-13-ynoic acid 2-(N,N-dimethylamino)-ethyl ester;

5c-9α,11α,15(S)-trihydroxy-19,20-dinor-18-cyclopentyl-prost-5-en-13-ynoic acid 2-(N,N-dimethylamino)-ethyl ester;

5c-9α,11α,15(R)-trihydroxy-16(S)-fluoro-19,20-dinor-18-cyclohexyl-prost-5-en-13-ynoic acid 2-(N,N-dimethylamino)-ethyl ester 5c-9α,11α,15(R,S)-trihydroxy-16(S)-fluoro-19,20-dinor-18-cyclohexyl-prost-5-en-13-ynoic acid 2-(N,N-dimethylamino)-ethyl ester 5c-9α,11α,15(S)-trihydroxy-18,19,20-trinor-17-cyclohexyl-prost-5-en-13-ynoic acid 2-(N,N-dimethylamino)-ethyl ester;

5c-9α,11α,15(S)-trihydroxy-18,19,20-trinor-17-cyclopentyl-prost-5-en-13-ynoic acid 2-(N,N-dimethylamino)-ethyl ester;

5c-9α,11α,15(R)-trihydroxy-16(S)-fluoro-18,19,20-trinor-17-cyclohexyl-prost-5-en-13-ynoic acid 2-(N,N-dimethylamino)-ethyl ester 5c-9α,11α,15(R,S)-trihydroxy-16(S)-fluoro-18,19,20-trinor-17-cyclohexyl-prost-5-en-13-ynoic acid 2-(N,N-dimethylamino)-ethyl ester 5c-9α,11α,15(R)-trihydroxy-16(S)-fluoro-18,19,20-trinor-17-cyclopentyl-prost-5-en-13-ynoic acid 2-(N,N-dimethylamino)-ethyl ester;

5c-9α,11α,15(R,S)-trihydroxy-16(S)fluoro-18,19,20-trinor-17-cyclopentyl-prost-5-en-13-ynoic acid 2-(N,N-dimethylamino)-ethyl ester 5c-9α,11α,15(S)-trihydroxy-17,18,19,20-tetranor-16-cyclohexyl-prost-5-en-13-ynoic acid 2-(N,N-dimethylamino)-ethyl ester;

5c-9α,11α,15(S)-trihydroxy-17,18,19,20-tetranor-16-cyclopentyl-prost-5-en-13-ynoic acid 2-(N,N-dimethylamino)-ethyl ester;

5c-9α,11α,15(R)-trihydroxy-16(S)-fluoro-17,18,19,20-tetranor-16-cyclohexyl-prost-5-en-13-ynoic acid 2-(N,N-dimethylamino)-ethyl ester 5c-9α,11α,15(R,S)-trihydroxy-16(S)-fluoro-17,18,19,20-tetranor-16-cyclohexyl-prost-5-en-13-ynoic acid 2-(N,N-dimethylamino)-ethyl ester;

5c-9α,11α,15(R)-trihydroxy-16(S)-fluoro-16-methyl-18,19,20-trinor-17-cyclohexyl-prost-5-en-13-ynoic acid 2-(N,N-dimethylamino)-ethyl ester;

5c-9α,11α,15(R,S)-trihydroxy-16(S)-fluoro-16-methyl-18,19,20-trinor-17-cyclohexyl-prost-5-en-13-ynoic acid 2-(N,N-dimethylamino)-ethyl ester;

5c-9α,11α,15(R)-trihydroxy-16(R)-fluoro-16-methyl-18,19,20-trinor-17-cyclohexyl-prost-5-en-13-ynoic acid 2-(N,N-dimethylamino)-ethyl ester;

5c-9α,11α,15(S)-trihydroxy-20-nor-19-cyclohexyl-prost-5-en-13-ynoic acid 2-(N,N-dimethylamino)-ethyl amide;

5c-9α,11α,15(S)-trihydroxy-20-nor-19-cyclopentyl-prost-5-en-13-ynoic acid 2-(N,N-dimethylamino)-ethyl amide;

5c-9α,11α,15(R)-trihydroxy-16(S)-fluoro-20-nor-19-cyclohexyl-prost-5-en-13-ynoic acid 2-(N,N-dimethyl amino)-ethyl amide;

5c-9α,11α,15(R,S)-trihydroxy-16(S)-fluoro-20-nor-19-cyclohexyl-prost-5-en-13-ynoic acid 2-(N,N-dimethylamino)-ethyl amide 5c-9α,11α,15(S)-trihydroxy-19,20-dinor-18-cyclohexyl-prost-5-en-13-ynoic acid 2-(N,N-dimethylamino)-ethyl amide;

5c-9α,11α,15(S)-trihydroxy-19,20-dinor-18-cyclopentyl-prost-5-en-13-ynoic acid 2-(N,N-dimethylamino)-ethyl amide;

5c-9α,11α,15(R)-trihydroxy-16(S)-fluoro-19,20-dinor-18-cyclohexyl-prost-5-en-13-ynoic acid 2-(N,N-dimethylamino)-ethyl amide 5c-9α,11α,15(R,S)-trihydroxy-16(S)-fluoro-19,20-dinor-18-cyclohexyl-prost-5-en-13-ynoic acid 2-(N,N-dimethylamino)-ethyl amide 5c-9α,11α,15(S)-trihydroxy-18,19,20-trinor-17-cyclohexyl-prost-5-en-13-ynoic acid 2-(N,N-dimethylamino)-ethyl amide;

5c-9α,11α,15(S)-trihydroxy-18,19,20-trinor-17-cyclopentyl-prost-5-en-13-ynoic acid 2-(N,N-dimethylamino)-ethyl amide;

5c-9α,11α,15(R)-trihydroxy-16(S)-fluoro-18,19,20-trinor-17-cyclohexyl-prost-5-en-13-ynoic acid 2-(N,N-dimethylamino)-ethyl amide 5c-9α,11α,15(R,S)-trihydroxy-16(S)-fluoro-18,19,20-trinor-17-cyclohexyl-prost-5-en-13-ynoic acid 2-(N,N-dimethylamino)-ethyl amide 5c-9α,11α,15(R)-trihydroxy-16(S)-fluoro-18,19,20-trinor-17-cyclopentyl-prost-5-en-13-ynoic acid 2-(N,N-dimethylamino)-ethyl amide;

5c-9α,11α,15(R,S)-trihydroxy-16(S)fluoro-18,19,20-trinor-17-cyclopentyl-prost-5-en-13-ynoic acid 2-(N,N-dimethylamino)-ethyl amide 5c-9α,11α,15(S)-trihydroxy-17,18,19,20-tetranor-16-cyclohexyl-prost-5-en-13-ynoic acid 2-(N,N-dimethylamino)-ethyl amide;

5c-9α,11α,15(S)-trihydroxy-17,18,19,20-tetranor-16-cyclopentyl-prost-5-en-13-ynoic acid 2-(N,N-dimethylamino)-ethyl amide;

5c-9α,11α,15(R)-trihydroxy-16(S)-fluoro-17,18,19,20-tetranor-16-cyclohexyl-prost-5-en-13-ynoic acid 2-(N,N-dimethylamino)-ethyl amide 5c-9α,11α,15(R,S)-trihydroxy-16(S)-fluoro-17,18,19,20-tetranor-16-cyclohexyl-prost-5-en-13-ynoic acid 2-(N,N-dimethylamino)-ethyl amide;

5c-9α,11α,15(R)-trihydroxy-16(S)-fluoro-16-methyl-18,19,20-trinor-17-cyclohexyl-prost-5-en-13-ynoic acid 2-(N,N-dimethylamino)-ethyl amide;

5c-9α,11α,15(R,S)-trihydroxy-16(S)-fluoro-16-methyl-18,19,20-trinor-17-cyclohexyl-prost-5-en-13-ynoic acid 2-(N,N-dimethylamino)-ethyl amide;

5c-9α,11α,15(R)-trihydroxy-16(R)-fluoro-16-methyl-18,19,20-trinor-17-cyclohexyl-prost-5-en-13-ynoic acid 2-(N,N-dimethylamino)-ethyl amide; and 5c-9α,11α,15(R,S)-trihydroxy-16(S)-fluoro-18,19,20-trinor-17-cyclohexyl-prost-5-en-13-ynoic acid piperazinyl-N-methylene amide.

EXAMPLE 5

CuCl (0.017 g) was added to a solution of 1.373 g of dicyclohexylcarbodiimide (DCC) in 0.661 g of 2-ethoxy-ethanol cooled at 0° C. The mixture was stirred for about 1 hour at 0° C., then it was allowed to rise to the room temperature and kept at this temperature for 24 hours. The mixture was then diluted with hexane (5 ml), filtered on silica gel and washed with hexane.

The solvent was removed to obtain 1.00 g of pure dicyclohexyl-2-ethoxy-ethylisourea. This product was dissolved in 10 ml of THF (distilled on CaCl$_2$) and added to a solution of 5c-9α,11α,15(S)-trihydroxy-18,19,20-trinor-17-cyclohexyl-prost-5-en-13-ynoic acid (1 g) in 10 ml of dry THF.

The mixture was warmed to 60° C. and keep at this temperature for 6 hours. The solvent was removed under vacuum and the crude product thus obtained was purified on silica gel by using a mixture of ethyl acetate/cyclohexane=70/30 as eluent. Pure 5c-9α,11α,15(S)-trihydroxy-18,19,20-trinor-17-cyclohexyl-prost-5-en-13-ynoic acid 2-ethoxy-ethyl ester (0.850 g) was collected: $[\alpha]_D=+29.7$; $[\alpha]_{365}=+97.4$ (C=1 EtOH).

By proceeding analogously the following compounds were obtained:

5c-9α,11α,15(S)-trihydroxy-20-nor-19-cyclohexyl-prost-5-en-13-ynoic acid 2-ethoxy-ethyl ester; $[\alpha]_D=+21.2$ 5c-9α,11α,15(S)-trihydroxy-20-nor-19-cyclopentyl-prost-5-en-13-ynoic acid 2-ethoxy-ethyl ester; $[\alpha]_D=+27$ 5c-9α,11α,15(R)-trihydroxy-16(S)-fluoro-20-nor-19-cyclohexyl-prost-5-en-13-ynoic acid 2-ethoxy-ethyl ester; $[\alpha]_D=+28.2$ 5c-9α,11α,15(R,S)-trihydroxy-16(S)-fluoro-20-nor-19-cyclohexyl-prost-5-en-13-ynoic acid 2-ethoxy-ethyl ester; $[\alpha]_D=+29.6$ 5c-9α,11α,15(S)-trihydroxy-19,20-dinor-18-cyclohexyl-prost-5-en-13-ynoic acid 2-ethoxy-ethyl ester; $[\alpha]_D=+31.7$ 5c-9α,11α,15(S)-trihydroxy-19,20-dinor-18-cyclopentyl-prost-5-en-13-ynoic acid 2-ethoxy-ethyl ester; $[\alpha]_D=+32.6$ 5c-9α,11α,15(R)-trihydroxy-16(S)-fluoro-19,20-dinor-18-cyclohexyl-prost-5-en-13-ynoic acid 2-ethoxy-ethyl ester; $[\alpha]_D=+18$ 5c-9α,11α,15(R,S)-trihydroxy-16(S)-fluoro-19,20-dinor-18-cyclohexyl-prost-5-en-13-ynoic acid 2-ethoxy-ethyl ester; $[\alpha]_D=+22$ 5c-9α,11α,15(S)-trihydroxy-18,19,20-trinor-17-cycloheptyl-prost-5-en-13-ynoic acid 2-ethoxy-ethyl ester; $[\alpha]_D=+19.2$ 5c-9α,11α,15(S)-trihydroxy-18,19,20-trinor-17-cyclopentyl-prost-5-en-13-ynoic acid 2-ethoxy-ethyl ester; $[\alpha]_D=+22.2$ 5c-9α,11α,15(R)-trihydroxy-16(S)-fluoro-18,19,20-trinor-17-cyclohexyl-prost-5-en-13-ynoic acid 2-ethoxy-ethyl ester; $[\alpha]_D=+14.2$ 5c-9α,11α,15(R,S)-trihydroxy-16(S)-fluoro-18,19,20-trinor-17-cyclohexyl-prost-5-en-13-ynoic acid 2-ethoxy-ethyl ester; $[\alpha]_D=+17.2$ 5c-9α,11α,15(R)-trihydroxy-16(S)-fluoro-18,19,20-trinor-17-cyclopentyl-prost-5-en-13-ynoic acid 2-ethoxy-ethyl ester; $[\alpha]_D=+14.8$ 5c-9α,11α,15(R,S)-trihydroxy-16(S)fluoro-18,19,20-trinor-17-cyclopentyl-prost-5-en-13-ynoic acid 2-ethoxy-ethyl ester; $[\alpha]_D=+24$ 5c-9α,11α,15(S)-trihydroxy-17,18,19,20-tetranor-16-cyclohexyl-prost-5-en-13-ynoic acid 2-ethoxy-ethyl ester; $[\alpha]_D=+38.6$ 5c-9α,11α,15(S)-trihydroxy-17,18,19,20-tetranor-16-cyclopentyl-prost-5-en-13-ynoic acid 2-ethoxy-ethyl ester; $[\alpha]_D=+41.2$ 5c-9α,11α,15(R)-trihydroxy-16(S)-fluoro-17,18,19,20-tetranor-16-cyclohexyl-prost-5-en-13-ynoic acid 2-ethoxy-ethyl ester; $[\alpha]_D=+16$ 5c-9α,11α,15(R,S)-trihydroxy-16(S)-fluoro-17,18,19,20-tetranor-16-cyclohexyl-prost-5-en-13-ynoic acid 2-ethoxy-ethyl ester; $[\alpha]_D=+22.7$ 5c-9α,11α,15(R)-trihydroxy-16(S)-fluoro-16-methyl-18,19,20-trinor-17-cyclohexyl-prost-5-en-13-ynoic acid 2-ethoxy-ethyl ester; $[\alpha]_D=+34.6$ 5c-9α,11α,15(R,S)-trihydroxy-16(S)-fluoro-16-methyl-18,19,20-trinor-17-cyclohexyl-prost-5-en-13-ynoic acid 2-ethoxy-ethyl ester; $[\alpha]_D=+39.2$ 5c-9α,11α,15(R)-trihydroxy-16(R)-fluoro-16-methyl-18,19,20-trinor-17-cyclohexyl-prost-5-en-13-ynoic acid 2-ethoxy-ethyl ester; $[\alpha]_D=+46$ 5c-9α,11α,15(S)-trihydroxy-20-nor-19-cyclohexyl-prost-5-en-13-ynoic acid 2-(N,N-dimethylamino)-ethyl ester;

5c-9α,11α,15(S)-trihydroxy-20-nor-19-cyclopentyl-prost-5-en-13-ynoic acid 2-(N,N-dimethylamino)-ethyl ester;

5c-9α,11α,15(R)-trihydroxy-16(S)-fluoro-20-nor-19-cyclohexyl-prost-5-en-13-ynoic acid 2-(N,N-dimethylamino)-ethyl ester;

5c-9α,11α,15(R,S)-trihydroxy-16(S)-fluoro-20-nor-19-cyclohexyl-prost-5-en-13-ynoic acid 2-(N,N-dimethylamino)-ethyl ester 5c-9α,11α,15(S)-trihydroxy-19,20-dinor-18-cyclohexyl-prost-5-en-13-ynoic acid 2-(N,N-dimethylamino)-ethyl ester;

5c-9α,11α,15(S)-trihydroxy-19,20-dinor-18-cyclopentyl-prost-5-en-13-ynoic acid 2-(N,N-dimethylamino)-ethyl ester;

5c-9α,11α,15(R)-trihydroxy-16(S)-fluoro-19,20-dinor-18-cyclohexyl-prost-5-en-13-ynoic acid 2-(N,N-dimethylamino)-ethyl ester 5c-9α,11α,15(R,S)-trihydroxy-B 16(S)-fluoro-19,20-dinor-18-cyclohexyl-prost-5-en-13-ynoic acid 2-(N,N-dimethylamino)-ethyl ester 5c-9α,11α,15(S)-trihydroxy-18,19,20-trinor-17-cyclohexyl-prost-5-en-13-ynoic acid 2-(N,N-dimethylamino)-ethyl ester;

5c-9α,11α,15(S)-trihydroxy-18,19,20-trinor-B 17-cyclopentyl-prost-5-en-13-ynoic acid 2-(N,N-dimethyl amino)-ethyl ester;

5c-9α,11α,15(R)-trihydroxy-16(S)-fluoro-18,19,20-tri-
nor-17-cyclohexyl-prost-5-en-13-ynoic acid 2-(N,N-
dimethylamino)-ethyl ester 5c-9α,11α,15(R,S)-trihydroxy-16(S)-fluoro-18,19,20-tri-
nor-17-cyclohexyl-prost-5-en-13-ynoic acid 2-(N,N-
dimethylamino)-ethyl ester 5c-9α,11α,15(R)-trihydroxy-16(S)-fluoro-18,19,20-tri-
nor-17-cyclopentyl-prost-5-en-13-ynoic acid 2-(N,N-
dimethylamino)-ethyl ester;

5c-9α,11α,15(R,S)-trihydroxy-16(S)fluoro-18,19,20-tri-
nor-17-cyclopentyl-prost-5-en-13-ynoic acid 2-(N,N-
dimethylamino)-ethyl ester 5c-9α,11α,15(S)-trihydroxy-17,18,19,20-tetranor-16-
cyclohexyl-prost-5-en-13-ynoic acid 2-(N,N-dime-
thylamino)-ethyl ester;

5c-9α,11α,15(S)-trihydroxy-17,18,19,20-tetranor-16-
cyclopentyl-prost-5-en-13-ynoic acid 2-(N,N-dime-
thylamino)-ethyl ester;

5c-9α,11α,15(R)-trihydroxy-16(S)-fluoro-17,18,19,20-
tetranor-16-cyclohyxyl-prost-5-en-13-ynoic acid 2-
(N,N-dimethylamino)-ethyl ester 5c-9α,11α,15(R,S)-trihydroxy-16(S)-fluoro-17,18,19,20-
tetranor-16-cyclohexyl-prost-5-en-13-ynoic acid 2-
(N,N-dimethylamino)-ethyl ester;

5c-9α,11α,15(R)-trihydroxy-16(S)-fluoro-16-methyl-
18,19,20-trinor-17-cyclohexyl-prost-5-en-13-ynoic
acid 2-(N,N-dimethylamino)-ethyl ester;

5c-9α,11α,15(R,S)-trihydroxy-16(S)-fluoro-16-methyl-
18,19,20-trinor-17-cyclohexyl-prost-5-en-13-ynioc
acid 2-(N,N-dimethylamino)-ethyl ester; and 5c-9α,11α,15(R)-trihydroxy-16(R)-fluoro-16-methyl-
18,19,20-trinor-17-cyclohexyl-prost-5-en-13-ynoic
acid 2-(N,N-dimethylamino)-ethyl ester.

EXAMPLE 6

A solution of 5c-9-oxo-11α,15(S)-dihydroxy-16(R)-fluoro-20-ethyl-prost-5-en-13-ynoic acid amide 11,15-bis-THP-ether (0.50 g) in acetone (10 ml), treated with 1N aqueous oxalic acid (10 ml), was refluxed for 7 hours. The acetone in excess was removed under vacuum and the solution was extracted with diethyl ether. The organic extract was concentrated and adsorbed on acid-washed silica-gel. Elutions with mixtures of benzene/diethyl ether afforded 0.20 g of 5c-9-oxo-15(S)-hydroxy-16(R)-fluoro-20-ethyl-prosta-5,10-dien-13-ynoic acid amide; $[\alpha]_D = +3.5$ (C=1 EtOH).

By using the same procedure, starting from the 9-oxo-11,15-bis-THP-ether intermediate derivatives obtained according to Example 3, the following compounds were prepared:

5c-9-oxo-15(S)-hydroxy-20-nor-19-cyclohexyl-prosta-5,10-dien-13-ynoic acid 2-ethoxy-ethyl ester; $[\alpha]_D = +2.8$ 5c-9-oxo-15(R)-hydroxy-20-nor-19-cyclopentyl-prosta-5,10-dien-13-ynoic acid 2-ethoxy-ethyl ester; $[\alpha]_D = +11.6$ 5c-9-oxo-15(R)-hydroxy-16(S)-fluoro-20-nor-19-cyclohexyl-prosta-5,10-dien-13-ynoic acid 2-ethoxy-ethyl ester; $[\alpha]_D = +6.7$ 5c-9-oxo-15(R,S)-hydroxy-16(S)-fluoro-20-nor-19-cyclohexyl-prosta-5,10-dien-13-ynoic acid 2-ethoxy-ethyl ester; $[\alpha]_D = +5.8$ 5c-9-oxo-15(S)-hydroxy-19,20-dinor-18-cyclohexyl-prosta-5,10-dien-13-ynoic acid 2-ethoxy-ethyl ester; $[\alpha]_D = +2.2$ 5c-9-oxo-15(S)-hydroxy-19,20-dinor-18-cyclopentyl-prosta-5,10-dien-13-ynoic acid 2-ethoxy-ethyl ester; $[\alpha]_D = +3.2$ 5c-9-oxo-15(R)-hydroxy-16(S)-fluoro-19,20-dinor-18-cyclohexyl-prosta-5,10-dien-13-ynoic acid 2-ethoxy-ethyl ester; $[\alpha]_D = +16.2$ 5c-9-oxo-15(R,S)-hydroxy-16(R)-fluoro-20-nor-19-cyclohexyl-prosta-5,10-dien-13-ynoic acid 2-ethoxy-ethyl ester; $[\alpha]_D = +6.6$ 5c-9-oxo-15(S)-hydroxy-18,19,20-trinor-17-cyclohexyl-prosta-5,10-dien-13-ynoic acid 2-ethoxy-ethyl ester; $[\alpha]_D = +2.4$ 5c-9-oxo-15(S)-hydroxy-18,19,20-trinor-17-cyclopentyl-prosta-5,10-dien-13-ynoic acid 2-ethoxy-ethyl ester; $[\alpha]_D = +2.9$ 5c-9-oxo-15(R)-hydroxy-16(S)-fluoro-18,19,20-trinor-17-cyclohexyl-prosta-5,10-dien-13-ynoic acid 2-ethoxy-ethyl ester; $[\alpha]_D = +2.9$ 5c-9-oxo-15(S,R)-hydroxy-16(S)-fluoro-18,19,20-trinor-17-cyclohexyl-prosta-5,10-dien-13-ynoic acid 2-ethoxy-ethyl ester; $[\alpha]_D = +9.9$ 5c-9-oxo-15(R)-hydroxy-16(S)-fluoro-18,19,20-trinor-17-cyclopentyl-prosta-5,10-dien-13-ynoic acid 2-ethoxy-ethyl ester; $[\alpha]_D = +12.1$ 5c-9-oxo-15(R,S)-hydroxy-16(S)-fluoro-18,19,20-trinor-17-cyclopentyl-prosta-5,10-dien-13-ynoic acid 2-ethoxy-ethyl ester; $[\alpha]_D = +7.7$ 5c-9-oxo-15(S)-hydroxy-17,18,19,20-tetranor-16-cyclohexyl-prosta-5,10-dien-13-ynoic acid 2-ethoxy-ethyl ester; $[\alpha]_D = +6.2$ 5c-9-oxo-15(S)-hydroxy-17,18,19,20-tetranor-16-cyclopentyl-prosta-5,10-dien-13-ynoic acid 2-ethoxy-ethyl ester; $[\alpha]_D = +5.8$ 5c-9-oxo-15(R)-hydroxy-16(S)-fluoro-17,18,19,20-tetranor-16-cyclohexyl-prosta-5,10-dien-13-ynoic acid 2-ethoxy-ethyl ester; $[\alpha]_D = +2.9$ 5c-9-oxo-15(R,S)-hydroxy-16(S)-fluoro-17,18,19,20-tetranor-16-cyclohexyl-prosta-5,10-dien-13-ynoic acid 2-ethoxy-ethyl ester; $[\alpha]_D = +5.1$.

EXAMPLE 7

5c-9α,11α,15(S)-Trihydroxy-18,19,20-trinor-17-cyclohexyl-prost-5-en-13-ynoic acid 2-(piperidino)-ethyl ester 11,15-bis THP-ether (0.720 g) was dissolved in 10 ml of dry CCl$_4$ and 0.5 ml of pyridine, then 0.1 ml of acetyl chloride were dropped into the solution.

The solution was stirred for about 2 hrs at room temperature and neutralized with 10% NaH$_2$PO$_4$ solution and extracted with ethyl ether.

The solvent was removed and the crude 5c-9α,11α,15(S)-trihydroxy-18,19,20-trinor-17-cyclohexyl-prost-5-en-13-ynoic acid 2-(piperidino)-ethyl ester 11,15-bis THP-ether 9-acetate was dissolved in a mixture of acetone (10 ml) and 1N oxalic acid (10 ml) and stirred 6 hours at 40° C. The reaction solution was diluted with 10 ml of water. The acetone was distilled and the mixture extracted with ethyl ether.

The crude product was purified on silica gel using ethyl acetate: cyclohexane=50:50 as eluent, thus affording 0.295 g of pure 5c-9α,11α,15(S)-trihydroxy-18,19,20-trinor-17-cyclohexyl-prost-5-en-13-ynoic acid 2-(piperidino)-ethyl ester 9 acetate $[\alpha]_D = +86.2$ (C=1 EtOH) By proceeding analogously the 9-acetate derivatives of all the compounds reported in Example 2 were obtained.

EXAMPLE 8

To a solution of 5c-9α,11α,15(R,S)-trihydroxy-16(S)-fluoro-18,19,20-trinor-17-cyclohexyl-prost-5-en-13-ynoic acid piperazinyl-N-methylene-amide (0.2 g) in 95% ethyl alcohol (5 ml) a stoichiometric amount of 1N HCl was added. The solvent was evaporated to dryness thus giving 5c-9α,11α,15(R,S)-trihydroxy-16(S)-fluoro-18,19,20-trinor-17-cyclohexyl-prost-5-en-13-ynoic acid piperazinyl-N-methylene-amide hydrochloride as white crystals, [α]$_D$= +23.7 (C=1 EtOH).

FORMULATION EXAMPLES

Formulation I: Tablet (1 mg)

Tablets, each weighing 80 mg and containing 1 mg of the active substance, are manufactured as follows:

Composition (for 100,000 tablets)

5c-9α,11α,15(S)-trihydroxy-20-nor-19-cyclohexyl-prost-5-en-13-ynoic acid 2-ethoxy-ethyl ester: 100 g
Lactose: 5000 g
Corn starch: 2720 g
Talc powder: 150 g
Magnesium stearate: 30 g 5c-9α,11α,15(S)-trihydroxy-20-nor-19-cyclohexyl-prost-5-en-13-ynoic acid 2-ethoxy-ethyl ester, the lactose and half the corn starch are mixed; the mixture is then forced through a sieve of 0.5 mm mesh size. Corn starch (18 g) is suspended in warm water (180 ml). The resulting paste is used to granulate the powder. The granules are dried, comminuted on a sieve of mesh size 1.4 mm, then the remaining quantity of starch, talc and magnesium stearate is added, carefully mixed and processed into tablets using punches of 5 mm diameter.

Formulation II: intramuscular injection

An injectable pharmaceutical composition was manufactured by dissolving 1-5 mg of 5c-9α,11α,15(S)-trihydroxy-20-nor-19-cyclohexyl-prost-5-en-13-ynoic acid 2-ethoxy-ethyl ester in sterile propyleneglycol (1-5 ml).

Formulation III: Capsule (1 mg)

| | |
|---|---|
| 5c-9α,11α,15(S)-trihydroxy-20-nor-19-cyclohexyl-prost-5-en-13-ynoic acid 2-ethoxy-ethyl ester | 1.0 mg |
| Lactose | 89.8 mg |
| Corn starch | 9.0 mg |
| Magnesium stearate | 0.2 mg |
| Total | 100.0 mg |

This formulation was encapsulated in two-piece hard gelatin capsules.

We claim:

1. Optically active or racemic prostaglandin derivatives of Formula (I)

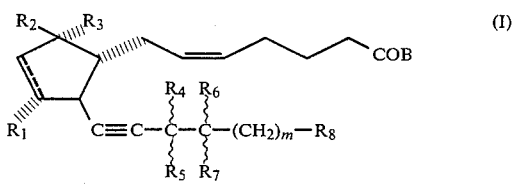

wherein
R is —O—(CH$_2$)$_n$—Z, wherein n is an integer of 2 to 4 and Z is a group

wherein each of R' and R'' is C$_1$-C$_6$ alkyl or R' and R'', taken together with the nitrogen atom to which they are linked, form a ring chosen from imidazolidinyl, piperidino, piperazinyl and morpholino or Z is a group —OR''', wherein R''' is C$_1$-C$_6$ alkyl;

the symbol represents a single bond, R$_1$ is hydroxy, R$_2$ is hydrogen and R$_3$ is hydroxy, benzoyloxy or C$_2$-C$_6$ alkanoyloxy, or R$_2$ and R$_3$, taken together, form an oxo group; or the symbol represents a double bond, R$_1$ is hydrogen and R$_2$ and R$_3$, taken together, form an oxo group, one of R$_4$ and R$_5$ is hydroxy and the other is hydrogen; each of R$_6$ and R$_7$ is, independently, hydrogen, C$_1$-C$_4$ alkyl or fluorine;

m is zero, 1 or 2;

R$_8$ is cyclopentyl, cyclohexyl or cycloheptyl, and the pharmaceutically or veterinarily acceptable salts thereof.

2. A compound according to claim 1, wherein R is —O—(CH$_2$)$_n$—Z, wherein n is 2 or 3 and Z is a group

wherein each of R' and R'' is C$_1$-C$_4$ alkyl or R' and R'', taken together with the nitrogen atom to which they are linked, are piperidino or morpholino or Z is a group —OR''', wherein R''' is C$_1$-C$_4$ alkyl;

the symbol represents a single bond, R$_1$ is hydroxy, R$_2$ is hydrogen and R$_3$ is hydroxy or C$_2$-C$_6$ alkanoyloxy, or R$_2$ and R$_3$, taken together, form an oxo group;

one of R$_4$ and R$_5$ is hydroxy and the other is hydrogen; each of R$_6$ and R$_7$ is, independently, hydrogen, C$_1$-C$_4$ alkyl or fluorine;

m is zero, 1 or 2;

R$_8$ is cyclopentyl or cyclohexyl; and the pharmaceuticaly or veterinarily acceptable salts thereof.

3. A compound according to claim 2, wherein R is —O—(CH$_2$)$_n$—Z, wherein n is 2 or 3 and Z is a group

wherein each of R' and R'' is C$_1$-C$_4$ alkyl or R' and R'', taken together with the nitrogen atom to which they are linked are piperidino or morpholino or Z is a group —OR''', wherein R''' is C$_1$-C$_4$ alkyl;

the symbol represents a single bond, R$_1$ is hydroxy, R$_2$ is hydrogen and R$_3$ is hydroxy;

one of R$_4$ and R$_5$ is hydroxy and the other hydrogen; each of R$_6$ and R$_7$ is, independently, hydrogen, C$_1$-C$_4$ alkyl or fluorine;

m is zero, 1 or 2;

R$_8$ is cyclohexyl, and the pharmaceutically or veterinarily acceptable salts thereof.

4. A pharmaceutical composition suitable for controlling fertility in female patients, said composition comprising a therapeutically effective amount of a compound of claim 1, in association with a pharmaceutically acceptable carrier or diluent.

5. A method of controlling fertility in female patients, said method comprising administering to said patient a therapeutically effective amount of a compound of claim 1.

6. A method of controlling fertility in female patients, said method comprising administering to said patient a therapeutically effective amount of a pharmaceutical composition of claim 4.

7. A compound selected from the group consisting of:
5c-9α,11α,15(S)-trihydroxy-20-nor-19-cyclohexyl-prost-5-en-13-ynoic acid 2-ethoxy-ethyl ester;
5c-9α,11α,15(S)-trihydroxy-20-nor-19-cyclopentyl-prost-5-en-13-ynoic acid 2-ethoxy-ethyl ester;
5c-9α,11α,15(R)-trihydroxy-16(S)-fluoro-20-nor-19-cyclohexyl-prost-5en-13-ynoic acid 2-ethoxy-ethyl ester;
5c-9α,11α,15(R,S)-trihydroxy-16(S)-fluoro-20-nor-19-cyclohexyl-prost-5-en-13-ynoic acid 2-ethoxy-ethyl ester;
5c-9α,11α,15(S)-trihydroxy-19,20-dinor-18-cyclohexyl-prost-5-en-13-ynoic acid 2-ethoxy-ethyl ester; 5c-9α,11α,15(S)-trihydroxy-19,20-dinor-18-cyclopentyl-prost-5-en-13-ynoic acid 2-ethoxy-ethyl ester; 5c-9α,11α,15(R)-trihydroxy-16(S)-fluoro-19,20-dinor-18-cyclohexyl-prost-5-en-13-ynoic acid 2-ethoxy-ethyl ester;
5c-9α,11α,15(R,S)-trihydroxy-16(S)-fluoro-19,20-dinor-18-cyclohexyl-prost-5-en-13-ynoic acid 2-ethoxy-ethyl ester;
5c-9α,11α,15(S)-trihydroxy-18,19,20-trinor-17-cyclohexyl-prost-5-en-13-ynoic acid 2-ethoxy-ethyl ester;
5c-9α,11α,15(S)-trihydroxy-18,19,20-trinor-17-cyclopentyl-prost-5-en-13-ynoic acid 2-ethoxy-ethyl ester;
5c-9α,11α,15(R)-trihydroxy-16(S)-fluoro-18,19,20-trinor-17-cyclohexyl-prost-5-en-13-ynoic acid 2-ethoxy-ethyl ester;
5c-9α,11α,15(R,S)-trihydroxy-16(S)-fluoro-18,19,20-trinor-17-cyclohexyl-prost-5-en-13-ynoic acid 2-ethoxy-ethyl ester; 5c-9α,11α,15(R)-trihydroxy-16(S)-fluoro-18,19,20-trinor-17-cyclopentyl-prost-5en-13-ynoic acid 2-ethoxy-ethyl ester;
5c-9α,11α,15(R,S)-trihydroxy-16(S)fluoro-18,19,20-trinor-17-cyclopentyl-prost-5-en-13-ynoic acid 2-ethoxy-ethyl ester;
5c-9α,11α,15(S)-trihydroxy-17,18,19,20-tetranor-16-cyclohexyl-prost-5-en-13-ynoic acid 2-ethoxy-ethyl ester;
5c-9α,11α,15(S)-trihydroxy-17,18,19,20-tetranor-16-cyclopentyl-prost-5-en-13-ynoic acid 2-ethoxy-ethyl ester;
5c-9α,11α,15(R)-trihydroxy-16(S)-fluoro-17,18,19,20-tetranor-16-cyclohexyl-prost-5-en-13-ynoic acid 2-ethoxy-ethyl ester;
5c-9α,11α,15(R,S)-trihydroxy-16(S)-fluoro-17,18,19,20-tetranor-16-cyclohexyl-prost-5-en-13-ynoic acid 2-ethoxy-ethyl ester;
5c-9α,11α,15(R)-trihydroxy-16(S)-fluoro-16-methyl-18,19,20-trinor-17-cyclohexyl-prost-5-en13ynoic acid 2-ethoxy-ethyl ester;
5c-9α,11α,15(R,S)-trihydroxy-16(S)-fluoro-16-methyl-18,19,20-trinor-17-cyclohexyl-prost-5-en-13-ynoic acid 2-ethoxy-ethyl ester;
5c-9α,11α,15(R)-trihydroxy-16(R)-fluoro-16-methyl-18,19,20-trinor-17-cyclohexyl-prost-5-en-13-ynoic acid 2-ethoxy-ethyl ester;
5c-9α,11α,15(S)-trihydroxy-20-nor-19-cyclohexyl-prost-5-en-13-ynoic acid 2-morpholino-ethyl ester;
5c-9α,11α,15(S)-trihydroxy-20-nor-19-cyclopentyl-prost-5-en-13-ynoic acid 2-morpholino-ethyl ester;
5c-9α,11α,15(R)-trihydroxy-16(S)-fluoro-20-nor-19-cyclohexyl-prost-5-en-13-ynoic acid 2-morpholino-ethyl ester;
5c-9α,11α,15(R,S)-trihydroxy-16(S)-fluoro-20-nor-19-cyclohexyl-prost-5-en-13-ynoic acid 2-morpholino-ethyl ester;
5c-9α,11α,15(S)-trihydroxy-19,20-dinor-18-cyclohexyl-prost-5-en-13-ynoic acid 2-morpholino-ethyl ester;
5c-9α,11α,15(S)-trihydroxy-19,20-dinor-18-cyclopentyl-prost-5-en-13-ynoic acid 2-morpholino-ethyl ester;
5c-9α,11α15(R)-trihydroxy-16(S)-fluoro-19,20-dinor-18-cyclohexyl-prost-5-en-13-ynoic acid 2-morpholino-ethyl ester;
5c-9α,11α,15(R,S)-trihydroxy-16(S)-fluoro-19,20-dinor-18-cyclohexyl-prost-5-en-13-ynoic acid 2-morpholino-ethyl ester;
5c-9α,11α, 15(S)-trihydroxy-18,19,20-trinor-17-cyclohexyl-prost-5-en-13-ynoic acid 2-morpholino-ethyl ester;
5c-9α,11α, 15(S)-trihydroxy-18,19,20-trinor-17-cyclopentyl-prost-5-en-13-ynoic acid 2-morpholino-ethyl ester;
5c-9α,11α,15(R)-trihydroxy-16(S)-fluoro-18,19,20-trinor-17-cyclohexyl-prost-5-en-13-ynoic acid 2-morpholino-ethyl ester;
5c-9α,11α,15(R,S)-trihydroxy-16(S)-fluoro-18,19,20-trinor-17-cyclohexyl-prost-5-en-13-ynoic acid 2-morpholino-ethyl ester;
5c-9α,11α,15(R)-trihydroxy-16(S)-fluoro-18,19,20-trinor-17-cyclopentyl-prost-5-en-13-ynoic acid 2-morpholino-ethyl ester;
5c-9α,11α,15(R,S)-trihydroxy-16(S)fluoro-18,19,20-trinor-17-cyclopentyl-prost-5-en-13-ynoic acid 2-morpholino-ethyl ester;
5c-9α,11α,15(S)-trihydroxy-17,18,19,20-tetranor-16-cyclohexyl-prost-5-en-13-ynoic acid 2-morpholino-ethyl ester;
5c-9α,11α,15(S)-trihydroxy-17,18,19,20-tetranor-16-cyclopentyl-prost-5-en-13-ynoic acid 2-morpholino-ethyl ester;
5c-9α,11α,15(R)-trihydroxy-16(S)-fluoro-17,18,19,20-tetranor-16-cyclohexyl-prost-5-en-13-ynoic acid 2-morpholino-ethyl ester;
5c-9α,11α,15(R,S)-trihydroxy-16(S)-fluoro-17,18,19,20-tetranor-16-cyclohexyl-prost-5en-13-ynoic acid 2-morpholino-ethyl ester;
5c-9α,11α,15(R)-trihydroxy-16(S)-fluoro-16methyl-18,19,20-trinor-17-cyclohexyl-prost-5-en-13-ynoic acid 2-morpholino-ethyl ester;
5c-9α,11α,15(R,S)-trihydroxy-16(S)-fluoro-16-methyl-18,19,20-trinor-17-cyclohexyl-prost-5-en-13-ynoic acid 2-morpholino-ethyl ester;
5c-9α,11α,15(R)-trihydroxy-16(R)-fluoro-16-methyl-18,19,20-trinor-17-cyclohexyl-prost-5-en-13-ynoic acid 2-morpholino-ethyl ester;
5c-9α,11α,15(S)-trihydroxy-20-nor-19-cyclohexyl-prost-5-en-13-ynoic acid 2-piperidino-ethyl ester;
5c-9α, 11α,15(S)-trihydroxy-20-nor-19-cyclopentyl-prost-5-en-13-ynoic acid 2-piperidino-ethyl ester;
5c-9α,11α,15(R)-trihydroxy-16(S)-fluoro-20-nor-19-cyclohexyl-prost-5-en-3-ynoic acid 2-piperidino-ethyl ester; 5c-9α,11α,15(R,S)-trihydroxy-16(S)- fluoro-20-nor-19-cyclohexyl-prost-5-en-13-ynoic acid 2-piperidino-ethyl ester;

5c-9α,11α,15(S)-trihydroxy-19,20-dinor-18-cyclohexyl-prost-5-en-13-ynoic acid 2-piperidino-ethyl ester;

5c-9α,11α,15(S)-trihydroxy-19,20-dinor-18-cyclopentyl-prost-5-en-13-ynoic acid 2-piperidino-ethyl ester;

5c-9α,11α,15(R)-trihydroxy-16(S)-fluoro-19,20-dinor-18-cyclohexyl-prost-5-en-13-ynoic acid 2-piperidino-ethyl ester;

5c-9α,11α,15(R,S)-trihydroxy-16(S)-fluoro-19,20-dinor-18-cyclohexyl-prost-5-en-13-ynoic acid 2-piperidino-ethyl ester;

5c-9α,11α,15(S)-trihydroxy-18,19,20-trinor-17-cyclohexyl-prost-5-en-13-ynoic acid 2-piperidino-ethyl ester;

5c-9α,11α,15(S)-trihydroxy-18,19,20-trinor-17-cyclopentyl-prost-5-en-13-ynoic acid 2-piperidino-ethyl ester;

5c-9α,11α,15(R)-trihydroxy-16(S)-fluoro-18,19,20-trinor-17-cyclohexyl-prost-5-en-13-ynoic acid 2-piperidino-ethyl ester;

5c-9α,11α,15(R,S)-trihydroxy-16(S)-fluoro-18,19,20-trinor-17-cyclohexyl-prost-5-en-13-ynoic acid 2-piperidino-ethyl ester;

5c-9α,11α,15(R)-trihydroxy-16(S)-fluoro-18,19,20-trinor-17-cyclopentyl-prost-5-en-13-ynoic acid 2-piperidino-ethyl ester;

5c-9α,11α,15(R,S)-trihydroxy-16(S)-fluoro-18,19,20-trinor-17-cyclopentyl-prost-5-en-13-ynoic acid 2-piperidino-ethyl ester;

5c-9α,11α,15(S)-trihydroxy-17,18,19,20-tetranor-16-cyclohexyl-prost-5-en-13-ynoic acid 2-piperidino-ethyl ester;

5c-9α,11α,15(S)-trihydroxy-17,18,19,20-tetranor-16-cyclopentyl-prost-5-en-13-ynoic acid 2-piperidino-ethyl ester;

5c-9α,11α,15(R)-trihydroxy-16(S)-fluoro-17,18,19,20-tetranor-16-cyclohexyl-prost-5-en-13-ynoic acid 2-piperidino-ethyl ester;

5c-9α,11α,15(R,S)-trihydroxy-16(S)-fluoro-17,18,19,20-tetranor-16-cyclohexyl-prost-5-en-13-ynoic acid 2-piperidino-ethyl ester;

5c-9α,11α,15(R)-trihydroxy-16(S)-fluoro-16-methyl-18,19,20-trinor-17-cyclohexyl-prost-5-en-13-ynoic acid 2-piperidino-ethyl ester;

5c-9α,11α,15(R,S)-trihydroxy-16(S)-fluoro-16-methyl-18,19,20-trinor-17-cyclohexyl-prost-5-en-13ynoic acid 2-piperidino-ethyl ester;

5c-9α,11α,15(R)-trihydroxy-16(R)-fluoro-16-methyl-18,19,20-trinor-17-cyclohexyl-prost-5-en-13-ynoic acid 2-piperidino-ethyl ester;

5c-9α,11α,15(S)-trihydroxy-20-nor-19-cyclohexyl-prost-5-en-13-ynoic acid 2-(N,N-dimethylamino)-ethyl ester;

5c-9α,11α,15(S)-trihydroxy-20-nor-19-cyclopentyl-prost-5-en-13-ynoic acid 2-(N,N-dimethylamino)-ethyl ester;

5c-9α,11α,15(R)-trihydroxy-16(S)-fluoro-20-nor-19-cyclohexyl-prost-5-en-13-ynoic acid 2-(N,N-dimethylamino)-ethyl ester;

5c-9α,11α,15(R,S)-trihydroxy-16(S)-fluoro-20-nor-19-cyclohexyl-prost-5-en-13-ynoic acid 2-(N,N-dimethylamino)-ethyl ester;

5c-9α,11α,15(S)-trihydroxy-19,20-dinor-18-cyclohexyl-prost-5-en-13-ynoic acid 2-(N,N-dimethylamino)-ethyl ester;

5c-9α,11α,15(S)-trihydroxy-19,20-dinor-18-cyclopentyl-prost-5-en-13-ynoic acid 2-(N,N-dimethylamino)-ethyl ester;

5-c9α,11α,15(R)-trihydroxy-16(S)-fluoro-19,20--dinor-18-cyclohexyl-prost-5-en-13-ynoic acid 2-(N,N-dimethylamino)-ethyl ester;

5-c9α,11α,15(R,S)-trihydroxy-16(S)-fluoro-19,2018-cyclohexyl-prost-5-en-13-ynoic acid 2-(N,N-dimethylamino)-ethyl ester;

5c-9α,11α,15(S)-trihydroxy-18,19,20-trinor-17-cyclohexyl-prost-5-en-13-ynoic acid 2-(N,N-dimethylamino)-ethyl ester;

5c-9α,11α,15(S)-trihydroxy-18,19,20-trinor-17-cyclopentyl-prost-5-en-13-ynoic acid 2-(N,N-dimethyl amino)-ethyl ester;

5c-9α,11α,15(R)-trihydroxy-16(S)-fluoro-18,19,20-trinor-17-cyclohexyl-prost-5-en-13-ynoic acid 2-(N,N-dimethylamino)-ethyl ester;

5c-9α,11α,15(R,S)-trihydroxy-16(S)-fluoro-18,19,20-trinor-17-cyclohexyl-prost-5-en-13-ynoic acid 2-(N,N-dimethylamino)-ethyl ester;

5c-9α,11α,15(R)-trihydroxy-16(S)-fluoro-18,19,20-trinor-17-cyclopentyl-prost-5-en-13-ynoic acid 2-(N,N-dimethylamino)-ethyl ester;

5c-9α,11α,15(R,S)-trihydroxy-16(S)fluoro-18,19,20-trinor-17-cyclopentyl-prost-5-en-13-ynoic acid 2-(N,N-dimethylamino)-ethyl ester;

5c-9α,11α,15(S)-trihydroxy-17,18,19,20-tetranor-16-cyclohexyl-prost-5-en-13-ynoic acid 2(N,N-dimethylamino)-ethyl ester;

5c-9α,11α,15(S)-trihydroxy-17,18,19,20-tetranor-16-cyclopentyl-prost-5-en-13-ynoic acid 2-(N,N-dimethylamino)-ethyl ester;

5c-9α,11α,15(R)-trihydroxy-16(S)-fluoro-17,18,19,20-tetranor-16-cyclohexyl-prost-5-en-13-ynoic acid 2-(N,N-dimethylamino)-ethyl ester;

5c-9α,11α,15(R,S)-trihydroxy-16(S)-fluoro-17,18,19,20-tetranor-16-cyclohexyl-prost-5-en-13-ynoic acid acid 2-(N,N-dimethylamino)-ethyl ester;

5c-9α,11α,15(R)-trihydroxy-16(S)-fluoro-16-methyl-18,19,20-trinor-17-cyclohexyl-prost-5-en-13-ynoic acid 2-(N,N-dimethylamino)-ethyl ester;

5c-9α,11α,15(R,S)-trihydroxy-16(S)-fluoro-16-methyl-18,19,20-trinor-17-cyclohexyl-prost-5-en-13-ynoic acid 2-(N,N-dimethylamino)-ethyl ester;

5c-9α,11α,15(R)-trihydroxy-16(R)-fluoro-16-methyl-18,19,20-trinor-17-cyclohexyl-prost-5-en-13-ynoic acid 2-(N,N-dimethylamino)-ethyl ester;

5c-9-oxo-11α,15(S)-dihydroxy-20-nor-19-cyclohexyl-prost-5-en-13-ynoic acid 2-ethoxy-ethyl ester;

5c-9-oxo-11α,15(S)-dihydroxy-20-nor-19-cyclopentyl-prost-5-en-13-ynoic acid 2-ethoxy-ethyl ester;

5c-9-oxo-11α,15(R)-dihydroxy-16(S)-fluoro-20-nor-19-cyclohexyl-prost-5-en-13-ynoic acid 2-ethoxy-ethyl ester;

5c-9-oxo-11α,15(R,S)-dihydroxy-16(S)-fluoro-20-nor-19-cyclohexyl-prost-5-en-13-ynoic acid 2-ethoxy-ethyl ester;

5c-9-oxo-11α,15(S)-dihydroxy-19,20-dinor-18-cyclohexyl-prost-5-en-13-ynoic acid 2-ethoxy-ethyl ester;

5c-9-oxo-11α,15(S)-dihydroxy-19,20-dinor-18-cyclopentyl-prost-5-en-13-ynoic acid 2-ethoxy-ethyl ester;

5c-9-oxo-11α,15(R)-dihydroxy-16(S)-fluoro-19,20-dinor-18-cyclohexyl-prost-5-en-13-ynoic acid 2-ethoxy-ethyl ester;

5c-9-oxo-11α,15(R,S)-dihydroxy-16(S)-fluoro-19,20-dinor-18-cyclohexyl-prost-5-en-13-ynoic acid 2-ethoxy-ethyl ester;

5c-9-oxo-11α,15(S)-dihydroxy-18,19,20-trinor-17-cyclohexyl-prost-5-en-13-ynoic acid 2-ethoxy-ethyl ester;

5c-9-oxo-11α,15(S)-dihydroxy-18,19,20-trinor-17-cyclopentyl-prost-5-en-13-ynoic acid 2-ethoxy-ethyl ester;

5c-9-oxo-11α,15(R)-dihydroxy-16(S)-fluoro-18,19,20-trinor-17-cyclohexyl-prost-5-en-13-ynoic acid 2-ethoxy-ethyl ester;

5c-9-oxo-11α,15(R,S)-dihydroxy-16(S)-fluoro-18,19,20-trinor-17-cyclohexyl-prost-5-en-13-ynoic acid 2-ethoxy-ethyl ester;

5c-9-oxo-11α,15(R)-dihydroxy-16(S)-fluoro-18,19,20-trinor-17-cyclopentyl-prost-5-en-13-ynoic acid 2-ethoxy-ethyl ester;

5c-9-oxo-11α,15(R,S)-dihydroxy-16(S)-fluoro-18,19,20-trinor-17-cyclopentyl-prost-5-en-13-ynoic acid 2-ethoxy-ethyl ester;

5c-9-oxo-11α,15(S)-dihydroxy-17,18,19,20-tetranor-16-cyclohexyl-prost-5-en-13-ynoic acid 2-ethoxy-ethyl ester;

5c-9-oxo-11α,15(S)-dihydroxy-17,18,19,20-tetranor-16-cyclopentyl-prost-5-en-13-ynoic acid 2-ethoxy-ethyl ester;

5c-9-oxo-11α,15(R)-dihydroxy-16(S)-fluoro-17,18,19,20-tetranor-16-cyclohexyl-prost-5-en-13-ynoic acid 2-ethoxy-ethyl ester;

5c-9-oxo-11α,15(R,S)-dihydroxy-16(S)-fluoro-17,18,19,20-tetranor-16-cyclohexyl-prost-5-en-13-ynoic acid 2-ethoxy-ethyl ester;

5c-9-oxo-11α,15(R)-dihydroxy-16(S)-fluoro-16-methyl-18,19,20-trinor-17-cyclohexyl-prost-5-en-13-ynoic acid 2-ethoxy-ethyl ester;

5c-9-oxo-11α,15(R,S)-dihydroxy-16(S)-fluoro-16-methyl-18,19,20-trinor-17-cyclohexyl-prost-5-en-13-ynoic acid 2-ethoxy-ethyl ester; and 5c-9-oxo-11α,15(R)-dihydroxy-16(R)-fluoro-16-methyl-18,19,20-trinor-17-cyclohexyl-prost-5-en-13-ynoic acid 2-ethoxy-ethyl ester, and the pharmaceutically or veterinarily acceptable salts of the 2-(N,N-dimethylamino)-ethyl esters hereinbefore listed.

* * * * *

UNITED STATES PATENT AND TRADEMARK OFFICE
CERTIFICATE OF CORRECTION

PATENT NO. : 4,543,353
DATED : September 24, 1985
INVENTOR(S) : Faustini et al

It is certified that error appears in the above-identified patent and that said Letters Patent is hereby corrected as shown below:

In the formula in claim 1 delete "COB" and replace by
--COR--

Insert "---" at column 34 lines 7, 11, 34 and 58.

Column 36 line 67 delete "3-ynoic" and replace by
--13-ynoic--

Column 38 line 4 delete "5-c9  " and replace by
--5c-9 --

Column 38 line 7 delete and replace by --5c-9α, 11α, 15(R,S) -trihydroxy- 16(S)-fluoro-19,20-dinor-18- --

Signed and Sealed this

Thirteenth Day of May 1986

[SEAL]

Attest:

DONALD J. QUIGG

Attesting Officer

Commissioner of Patents and Trademarks